(12) United States Patent
Chappa et al.

(10) Patent No.: US 11,478,815 B2
(45) Date of Patent: Oct. 25, 2022

(54) COATING SYSTEMS FOR MEDICAL DEVICES

(71) Applicant: Surmodics, Inc., Eden Prairie, MN (US)

(72) Inventors: Ralph A. Chappa, Ham Lake, MN (US); Michael Militello, Eden Prairie, MN (US)

(73) Assignee: Surmodics, Inc., Eden Prairie, MN (US)

(*) Notice: Subject to any disclaimer, the term of this patent is extended or adjusted under 35 U.S.C. 154(b) by 0 days.

(21) Appl. No.: 17/149,390

(22) Filed: Jan. 14, 2021

(65) Prior Publication Data
US 2021/0220866 A1 Jul. 22, 2021

Related U.S. Application Data

(60) Provisional application No. 62/962,099, filed on Jan. 16, 2020.

(51) Int. Cl.
*B05C 11/10* (2006.01)
*A61L 29/08* (2006.01)
(Continued)

(52) U.S. Cl.
CPC ........ *B05C 11/1026* (2013.01); *A61L 29/085* (2013.01); *B05C 11/08* (2013.01); *A61L 2420/02* (2013.01); *B05C 1/0813* (2013.01)

(58) Field of Classification Search
CPC ... G01N 1/10; F17D 3/00; A61L 29/08; A61L 29/085; B05C 11/1026; A61M 25/10
See application file for complete search history.

(56) References Cited

U.S. PATENT DOCUMENTS

| 4,195,637 A | 4/1980 | Gruntzig et al. |
| 5,041,089 A | 8/1991 | Mueller et al. |
(Continued)

OTHER PUBLICATIONS

R1,Syringe 50mL Luer Lock Plastic PK30, 2014, Amazon, p. 1 (Year: 2014).*

(Continued)

*Primary Examiner* — Dah-Wei D. Yuan
*Assistant Examiner* — Andrew J Bowman
(74) *Attorney, Agent, or Firm* — Pauly, DeVries Smith & Deffner LLC

(57) ABSTRACT

Aspects herein relate to coating apparatus and methods for coating medical devices. In an embodiment, a coating system is included having a valve, a fluid supply reservoir in fluid communication with the valve, a reciprocating positive displacement pump in fluid communication with the valve, and a fluid applicator in fluid communication with the three-way valve. The valve can be configured to assume a first fluid transport state and a second fluid transport state, wherein the valve provides fluid communication between the fluid supply reservoir and the reciprocating positive displacement pump when in the first fluid transport state for filling of the reciprocating positive displacement pump, and wherein the valve provides fluid communication between the reciprocating positive displacement pump and the fluid applicator when in the second fluid transport state for applying a coating suspension to a medical device surface. Other embodiments are also included herein.

17 Claims, 11 Drawing Sheets

(51) Int. Cl.
*B05C 11/08* (2006.01)
*B05C 1/08* (2006.01)

(56) References Cited

U.S. PATENT DOCUMENTS

| | | |
|---|---|---|
| 5,087,246 A | 2/1992 | Smith |
| 5,318,587 A | 6/1994 | Davey |
| 5,382,234 A | 1/1995 | Cornelius et al. |
| 5,571,089 A | 11/1996 | Crocker |
| 5,776,101 A | 7/1998 | Goy |
| 5,807,331 A | 9/1998 | Den Heijer et al. |
| 5,882,336 A | 3/1999 | Janacek |
| 6,394,995 B1 | 5/2002 | Solar et al. |
| 6,517,515 B1 | 2/2003 | Eidenschink |
| 6,623,504 B2 | 9/2003 | Vrba et al. |
| 6,896,842 B1 | 5/2005 | Hamilton et al. |
| 7,034,765 B2 | 4/2006 | Fischer et al. |
| 7,163,523 B2 | 1/2007 | Devens, Jr. et al. |
| 7,470,547 B2 * | 12/2008 | Tisone ............... B01D 19/0047 436/180 |
| 8,889,760 B2 | 11/2014 | Kurdyumov et al. |
| 10,098,846 B2 | 10/2018 | Slager |
| 10,099,041 B2 | 10/2018 | Chappa et al. |
| 2007/0155906 A1 | 7/2007 | Hissink et al. |
| 2007/0260054 A1 | 11/2007 | Chudzik |
| 2012/0296274 A1 | 11/2012 | Slager |
| 2013/0052359 A1 * | 2/2013 | Ahmadi ............. B05C 11/1002 427/421.1 |
| 2018/0071499 A1 * | 3/2018 | Goto ................. A61M 25/1029 |
| 2018/0110903 A1 | 4/2018 | Slager et al. |

OTHER PUBLICATIONS

Ghonaim, Hassan M. et al., "N1,N12-Diacyl Spermines: SAR Studies on Non-viral Lipopolyamine Vectors for Plasmid DNA and siRNA Formulation," Pharmaceutical Research, vol. 27, No. 1, Jan. 2010 (p. 17-29) Oct. 30, 2009.

"Htsr Syringe pump and valve," HTSR Resources Microfluidic Syringe pump and 3 way valve features accessible at URL <https://www.htsresources.com/syringe-3way-valve/syringe-3wayvalve.php> 2015 (4 pages).

"HT-syringe-10ml Syringe pump with valve for disposable syringes," HTS Resources Microfluidic Syringe Pump Product description available at URL<https://www.htsresources.com/microfluidicsyringepump_3wayvalve.php> at least as early as Jun. 28, 2015 (3 pages).

Love, Kevin T. et al., "Lipid-like materials for low-dose, in vivo gene silencing," PNAS, Feb. 2, 2010, vol. 107, No. 5, 1864-1869 (7 pages).

* cited by examiner

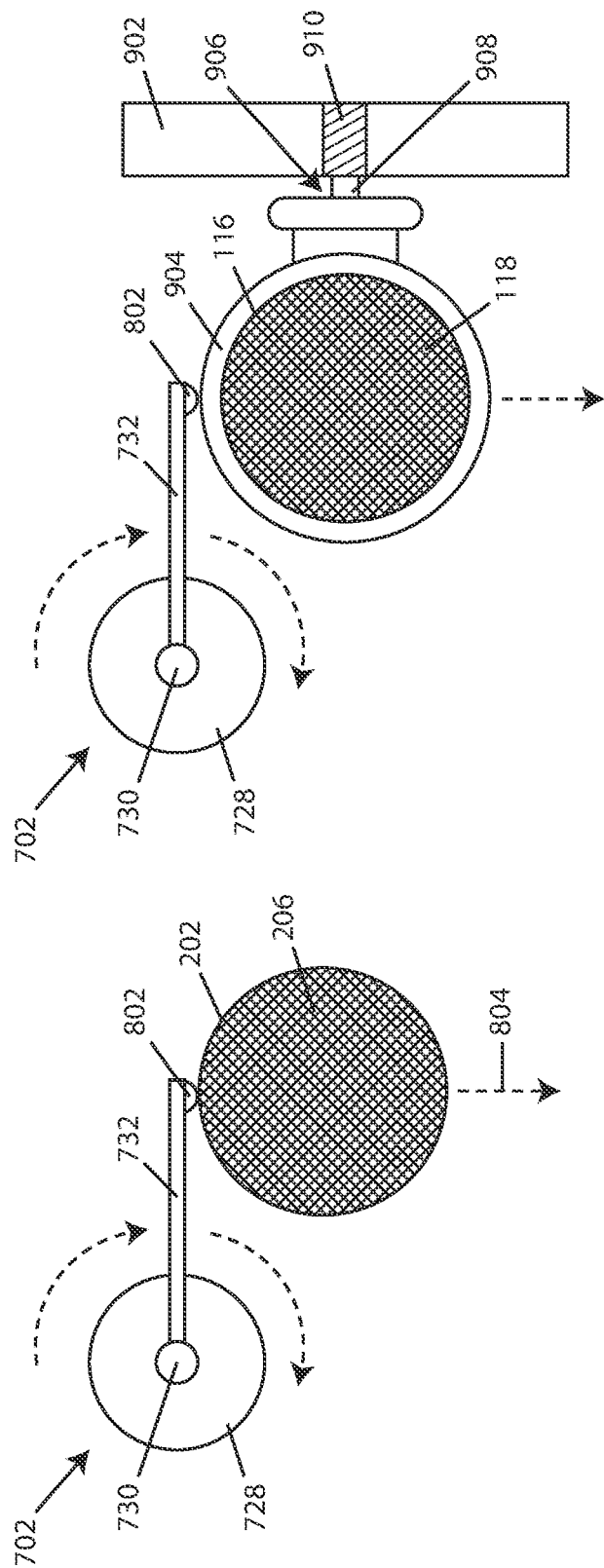

COATING SYSTEMS FOR MEDICAL DEVICES

This application claims the benefit of U.S. Provisional Application No. 62/962,099, filed Jan. 16, 2020, the content of which is herein incorporated by reference in its entirety.

FIELD

Embodiments herein relate to coating apparatus and methods for coating medical devices.

BACKGROUND

Functional improvements to implantable or insertable medical devices can be achieved by coating the surface of the device. For example, a coating formed on the surface of the device can provide improved lubricity, improved biocompatibility, or drug delivery properties to the surface. In turn, this can improve movement of the device in the body, extend the functional life of the device, or treat a medical condition near the site of implantation. However, various challenges exist for the design and use of coating apparatus designed to provide coatings to medical devices.

Traditional coating methods, such as dip coating, are often undesirable as they may result in flawed coatings that could compromise the function of the device or present problems during use. These methods can also result in coating inaccuracies, which can be manifested in variable amounts of the coated material being deposited on the surface of the device. When a drug is included in the coating material, it is often necessary to deliver precise amounts of the agent to the surface of the device to ensure that a subject receiving the coated device receives a proper dose of the agent. However, it has been difficult to achieve a great degree of consistency using traditional coating methods and machines.

SUMMARY

Aspects herein relate to coating apparatus and methods for coating medical devices. In an embodiment, a coating system is included having a valve, a fluid supply reservoir in fluid communication with the valve, a reciprocating positive displacement pump in fluid communication with the valve, and a fluid applicator in fluid communication with the three-way valve. The valve can be configured to assume a first fluid transport state and a second fluid transport state, wherein the valve provides fluid communication between the fluid supply reservoir and the reciprocating positive displacement pump when in the first fluid transport state for filling of the reciprocating positive displacement pump, and wherein the valve provides fluid communication between the reciprocating positive displacement pump and the fluid applicator when in the second fluid transport state for applying a coating suspension to a medical device surface.

In an embodiment, a method of operating a coating system for coating a medical device is included, the method can include actuating a valve to assume a first fluid transport state wherein the valve provides fluid communication between a fluid supply reservoir and a reciprocating positive displacement pump, conveying a coating suspension from the fluid supply reservoir to the reciprocating positive displacement pump through a first fluid flow path, actuating the valve to assume a second fluid transport state wherein the valve provides fluid communication between the reciprocating positive displacement pump and a fluid applicator, and conveying the coating suspension from the reciprocating positive displacement pump to the fluid applicator through a second fluid flow path.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 8 is a schematic top view of a striking assembly and a fluid supply reservoir in accordance with various embodiments herein.

FIG. 9 is a schematic top view of a striking assembly and a supply reservoir assembly in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Coatings are frequently applied onto the surfaces of various medical devices including, but not limited to, catheters and particularly balloon catheters. It is typically desirable for such coatings to be as uniform (in terms of thickness, composition, etc.) as possible. Also, it is desirable to coat device with minimal waste of active agents and with little exposure to human operators of coating equipment.

Embodiments herein can be used to apply uniform coatings, such as coatings including active agents, onto various medical devices, such as onto the balloons of drug coated or drug eluting balloon catheters, that have substantially uniform active agent concentrations along the length of the medical device. Various embodiments herein include a coating suspension being beneficially applied with a two-stage coating system wherein the first stage includes conveying a coating suspension from a supply reservoir to a pump and the second stage includes conveying the coating suspension from the pump to a coating applicator. In various embodiments, the two stages are configured to cycle automatically so as to eliminate the need for human intervention and exposure of the system operator to components of the coating suspension such as active agents thereof.

While not intending to be bound by theory, it is believed that suspension herein can be beneficially applied by passing through relatively narrow fluid conduits that are largely straight. It is believed that suspension herein can be beneficially applied by passing through relatively narrow fluid conduits that lack cavities or other points where the effective cross-section of the fluid flow path substantially increases.

Figure 1:
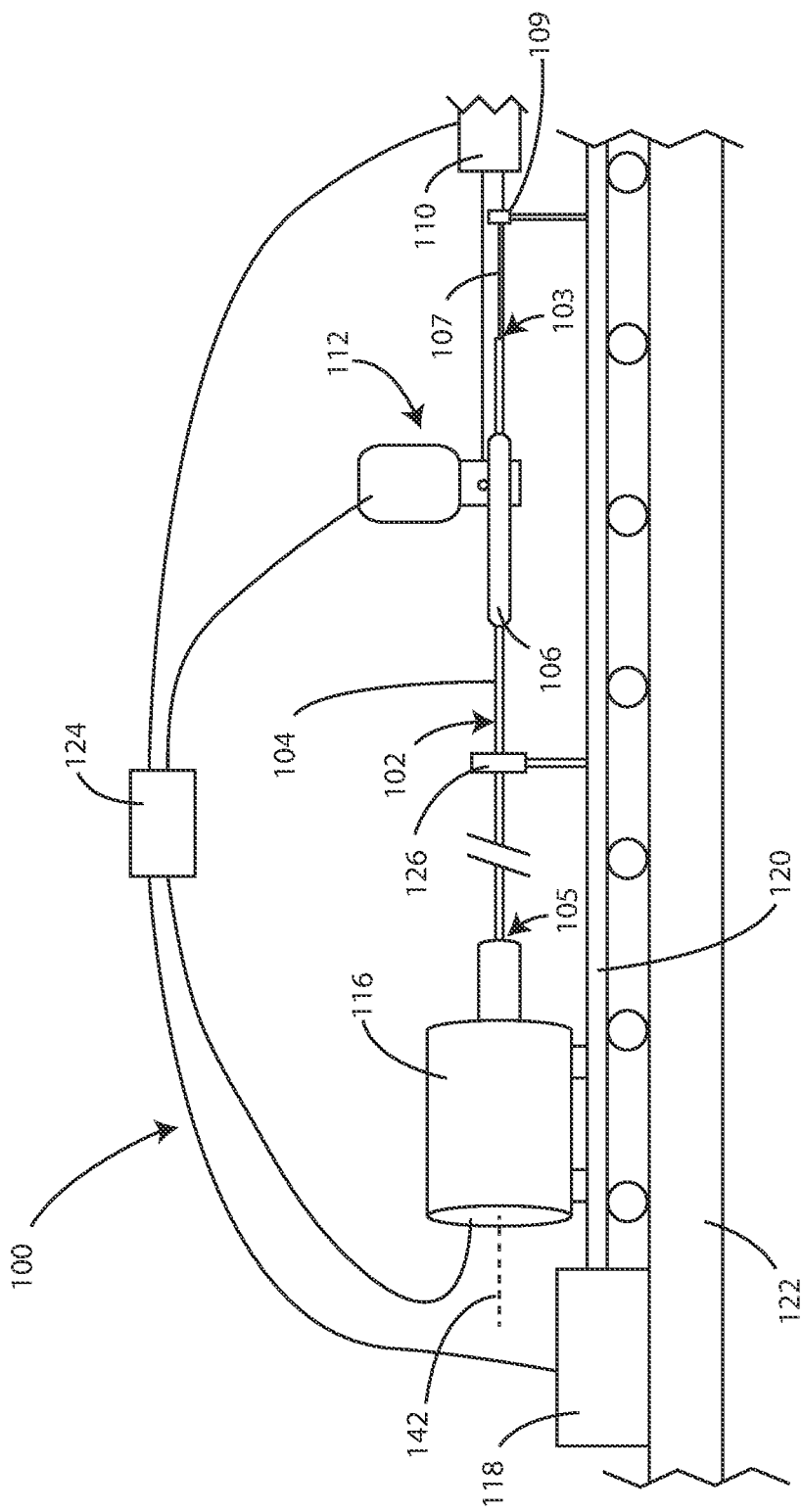
FIG. 1 is a schematic view of a coating apparatus in accordance with various embodiments herein.

Referring now to FIG. 1, a schematic side view is shown of a coating apparatus 100 in accordance with various embodiments herein. The orientation of elements of the coating apparatus 100 in this view are just provided by way of example and it will be appreciated that the orientation of individual components can be configured differently, such as reversed, as well as the orientation of the whole apparatus. The coating apparatus 100 is shown in conjunction with a medical device 102 (which could be a drug coated balloon catheter, or another cylindrical or rollable device). In this example, the medical device 102 can include a catheter shaft 104 and a balloon 106. The balloon 106 can assume a deflated configuration and an inflated configuration. The medical device 102 can include a distal end 103 and a proximal end 105. The medical device 102 can include a proximal end manifold (not shown).

The coating apparatus 100 can include a coating application unit 112. The coating application unit 112 can include various components including, but not limited to a two-part applicator. The coating apparatus 100 can further include, in some embodiments, an axial motion mechanism 110 (axial with respect to the axis of rotation of the balloon catheter and thus parallel to the lengthwise axis of the balloon catheter) that can function to move one or more components of the coating application unit 112. The axial motion mechanism 110 can include an electric motor and, in some cases, gears, belts and/or chains. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. However, it will be appreciated that in other embodiments, the coating application unit 112 can remain stationary.

Coating of the balloon 106 to make it drug coated can occur starting at the proximal end of the balloon and proceeding to the distal end. However, in other embodiments, coating of the balloon 106 can occur starting at the distal end of the balloon and proceeding to the proximal end. In some embodiments, coating can take place with a single pass of the coating application unit 112 with respect to the balloon. However, in other embodiments, multiple passes of the coating application unit with respect to the balloon can be made.

The coating application unit 112 can operate to pump a coating composition at a rate sufficient to apply about 0.5 µl to about 10 µl of the coating composition per millimeter of length of the balloon or other device to be coated. In some embodiments, the coating application unit 112 can operate to pump a coating composition at a rate sufficient to apply at least 0.05 µl, 0.1 µl, 0.3 µl, 0.5 µl, 0.8 µl, 1 µl, 1.25 µl, 1.5 µl, 1.75 or 2.00 µl of the coating composition per millimeter of length of the balloon or other device to be coated. In some embodiments, the rate can be sufficient to apply less than or equal to 10 µl, 9 µl, 8 µl, 7 µl, 6 µl, 5 µl, 4 µl, 3 or 2 µl of the coating composition per millimeter of length of the balloon or other device to be coated. In some embodiments, the rate can be sufficient to apply an amount falling within a range of 0.05 µl to 10 µl, or 0.1 µl to 9 µl, or 0.3 µl to 9 µl, or 0.5 µl to 8 µl, or 0.8 µl to 7 µl, or 1 µl to 6 µl, or 1.25 µl to 5 µl, or 1.5 µl to 4 µl, or 1.75 µl to 3 µl of the coating composition per millimeter of length of the balloon or other device to be coated.

The coating apparatus 100 can further include a rotation mechanism 116 (or rotating balloon catheter fixture). The rotation mechanism 116 can include an electric motor. In some embodiments, the rotation mechanism 116 can also include gears and/or belts, chains, etc.

The rotation mechanism 116 can be directly or indirectly coupled to the drug coated balloon catheter in order to rotate the medical device 102 around a rotation axis 142 (the lengthwise or major axis of the medical device 102). In some embodiments, the speed can be greater than or equal to 10 RPM, 30 RPM, 60 RPM, 90 RPM, 120 RPM, 150 RPM, 180 RPM, 210 RPM, 240 RPM, or 270 RPM. In some embodiments, the speed can be less than or equal to 1000 RPM, 900 RPM, 800 RPM, 700 RPM, 600 RPM, 500 RPM, 400 RPM, 300 RPM, 200 RPM, or 100 RPM. In some embodiments, the speed can fall within a range between any of the foregoing.

In some embodiments, a guide wire 107, passing through the central lumen of the catheter, can extend from the distal tip of the catheter and be inserted into a distal tip support ring 109 or guide. In this manner, the guide wire 107 can be used to support the distal tip of the balloon catheter to be coated while allowing the balloon catheter to rotate freely.

The coating apparatus 100 can further include, in some embodiments, an axial motion mechanism 118 which can be configured to move the medical device 102 in the direction of its lengthwise major axis. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. In some embodiments, the axial motion mechanism 118 can be a linear actuator. In some embodiments, the axial motion mechanism 118 can include an electric motor.

The coating apparatus 100 can further include a frame member 120 (in some embodiments this can also be referred to as an axial motion support rail). The frame member 120 can support other components of the coating apparatus 100 such as one or more guides 126. The frame member 120 can itself be support by a platform 122. The coating apparatus 100 can further include a controller 124 that can serve to control operation of the coating apparatus 100 including, specifically, coating application unit 112, axial motion mechanism 110, rotation mechanism 116, and axial motion mechanism 118. Further aspects of coating apparatus components are described in U.S. Pat. No. 10,099,041, the content of which is herein incorporated by reference.

Figure 2:
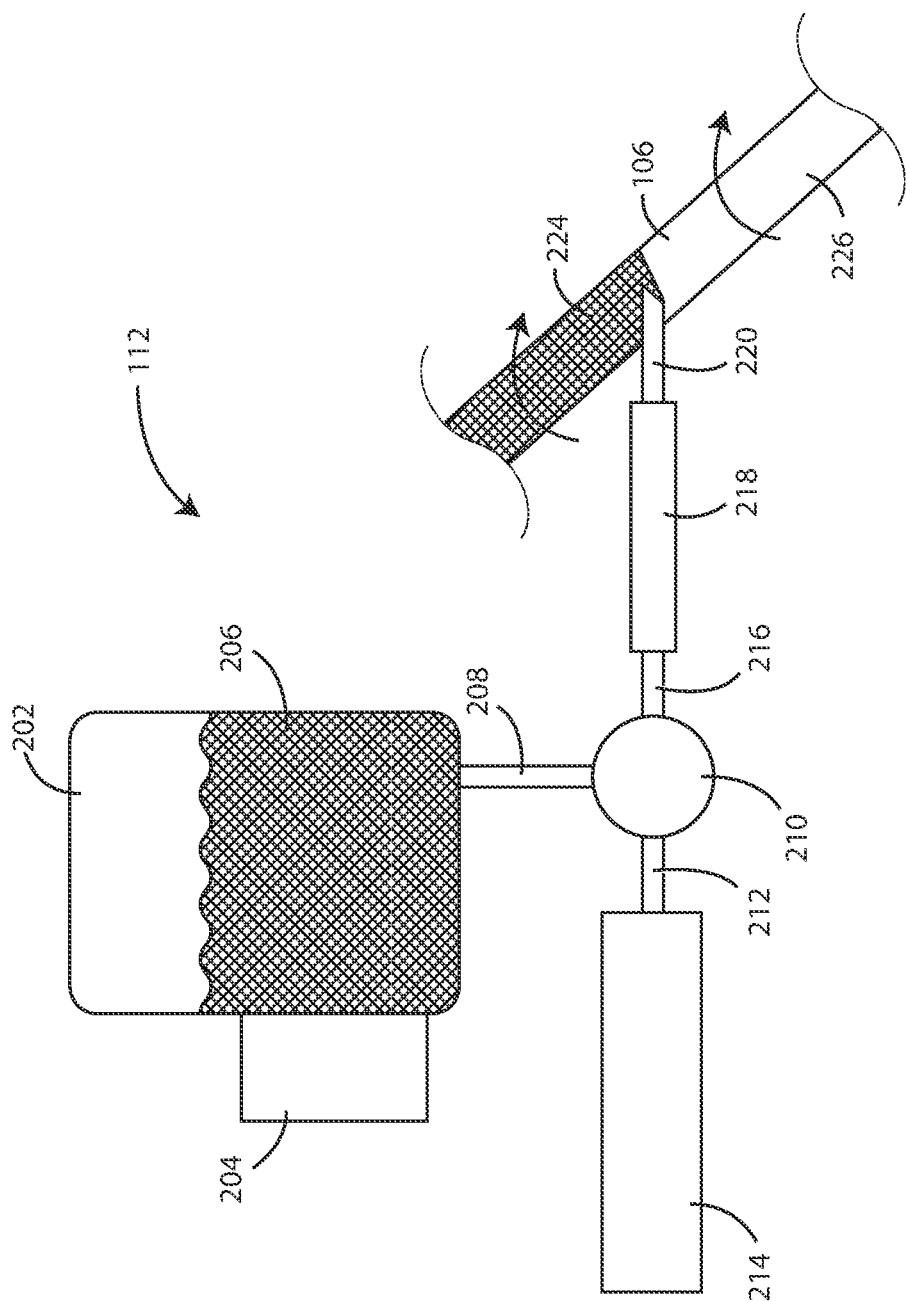
FIG. 2 is a schematic view of a coating application unit in accordance with various embodiments herein.

Referring now to FIG. 2, a schematic view of a coating application unit 112 is shown in accordance with various embodiments herein. FIG. 2 shows a balloon 106 being coated. The balloon 106 includes a coated portion 224 and an uncoated portion 226. The coating application unit 112 includes a fluid supply reservoir 202. The fluid supply reservoir 202 can include a coating suspension 206 disposed therein. In various embodiments, the coating application unit 112 can function to apply the coating suspension 206 to a medical device surface (exemplary medical devices are described in greater detail below). The coating application unit 112 also includes an agitation unit 204. The agitation unit 204 can serve to provide stirring, agitation, movement, or other energy to a coating suspension within the fluid supply reservoir 202. In some embodiments, the agitation unit 204 includes an electric motor and/or solenoid. The agitation unit 204 can drive a stirring bar or paddle either directly (e.g., a direct mechanical connection) or indirectly (such as with a magnetic force). In some embodiments the agitation unit 204 can include a striking member (or tapping member) to impact the fluid supply reservoir 202 and keep the suspension therein in a desirable state. In some embodiments the agitation unit 204 can include an ultrasonic stimulation/energy emitter keep the suspension within the fluid supply reservoir 202 in a desirable state. In some embodiments, the agitation unit 204 includes components that are purely outside of the fluid supply reservoir 202 (and therefore not in direct contact with the coating suspension 206 or fluid). However, in some embodiments, the agitation unit 204 can include at least one or more components that are inside the fluid supply reservoir 202 (such as a stir bar, paddle, etc.). While not intending to be bound by theory, in some scenarios it can be advantageous to have all agitation unit 204 components outside of the fluid supply reservoir 202 in order to avoid the inadvertent generation of particles through direct contact, rubbing, etc. In some cases, particles may serve as a seed (nucleation seed) for aggregates to form, which can result in adverse effects.

The coating application unit 112 also includes a fluid supply conduit 208. The coating application unit 112 also includes a valve 210. Various embodiments herein include many different types of valves. In some embodiments, the valve 210 is a three-way valve. In some embodiments, a three-way valve can be a three-way stopcock or the like. In some embodiments, the valve comprises a ball valve. In some embodiments, the valve can be a T-port valve. In some embodiments, the valve can be an L-port valve. The valve can include various components for actuation, such as actuator 350. In some embodiments, the actuator 350 can include a pneumatic diaphragm actuator, a pneumatic piston actuator, a hydraulic actuator, or an electric actuator (which can include an electric motor, such as an electric stepper motor). The actuator 350 can be used to move the valve 210 from one position or state to another.

The coating application unit 112 also includes a pump conduit 212. The coating application unit 112 also includes a pump, such as a reciprocating positive displacement pump 214. However, it will be appreciated that the pump can taken on various different forms. In some embodiments, the pump or reciprocating positive displacement pump is selected from the group consisting of a plunger pump, a piston pump, a diaphragm pump, and a syringe pump. In some embodiments, a reciprocating positive displacement pump can specifically be a single-acting reciprocating pump. In some embodiments, the pump can specifically be a syringe pump.

The coating application unit 112 also includes an applicator conduit 216. The coating application unit 112 also includes a fluid applicator 218

In various embodiments, the fluid supply reservoir 202 can be in fluid communication with the valve 210. In various embodiments, the valve 210 can be configured to assume a first fluid transport state and a second fluid transport state. In various embodiments, the valve 210 provides fluid communication between the fluid supply reservoir 202 and the reciprocating positive displacement pump 214 when it is in the first fluid transport state. This first fluid transport rate can be used for filling and/or draining of the reciprocating positive displacement pump 214. In various embodiments, the valve 210 also provides fluid communication between the reciprocating positive displacement pump 214 and the fluid applicator 218 when in the second fluid transport state. The second fluid transport state can be used for applying a coating suspension 206 to a medical device surface. The fluid applicator 218 can include an applicator tip 220.

A fluid flow pathway going through the fluid supply reservoir 202, valve 210, and the reciprocating positive displacement pump 214 can define a first fluid flow path, the first fluid flow path comprising an inner diameter of about 100 microns to about 2000 microns on average or at its narrowest point. In various embodiments, the first fluid flow path comprising an inner diameter of about 100, 200, 300, 400, 500, 750, 1000, 1250, 1500, 1750 or 2000 microns on average or at its narrowest point, or an inner diameter falling within a range between any of the foregoing. In some embodiments, the first fluid flow path is substantially the same inner diameter through its whole length. In some embodiments, the first fluid flow path substantially lacks expansional changes in cross-sectional area exceeding 50%. In some embodiments, the first fluid flow path substantially lacks expansional changes in cross-sectional area exceeding 10%. In some embodiments, the first fluid flow path lacks cavities.

The first fluid flow path can vary in length. In some embodiments, the first fluid flow path can be at least about 1, 2, 3, 4, 5, 8, 12, 15, 20, or 30 centimeters in length, or a length falling within a range between any of the foregoing.

A fluid flow pathway going through the reciprocating positive displacement pump 214, the valve 210, and the fluid applicator 218 define a second fluid flow path, the second fluid flow path comprising an inner diameter of about 100 microns to about 500 microns on average or at its narrowest point. In some embodiments, the second fluid flow path is substantially the same inner diameter through its whole length. In some embodiments, the second fluid flow path substantially lacks expansional changes in cross-sectional area exceeding 50%. In some embodiments, the second fluid flow path substantially lacks expansional changes in cross-sectional area exceeding 10%. In some embodiments, the second fluid flow path lacks cavities.

The second fluid flow path can vary in length. In some embodiments, the second fluid flow path can be at least about 1, 2, 3, 4, 5, 8, 12, 15, 20, or 30 centimeters in length, or a length falling within a range between any of the foregoing.

In some embodiments the second fluid flow path can be substantially straight. In some embodiments, the second fluid flow path does not turn by more than 30 degrees when the valve is in the second fluid transport state. In some embodiments, the second fluid flow path does not turn by more than 10 degrees when the valve is in the second fluid transport state.

In various embodiments, the first fluid flow path and the second fluid flow path can partially overlap (e.g., share a common portion). However, in some embodiments the first fluid flow path and the second fluid flow path can be entirely separate.

Figure 3:
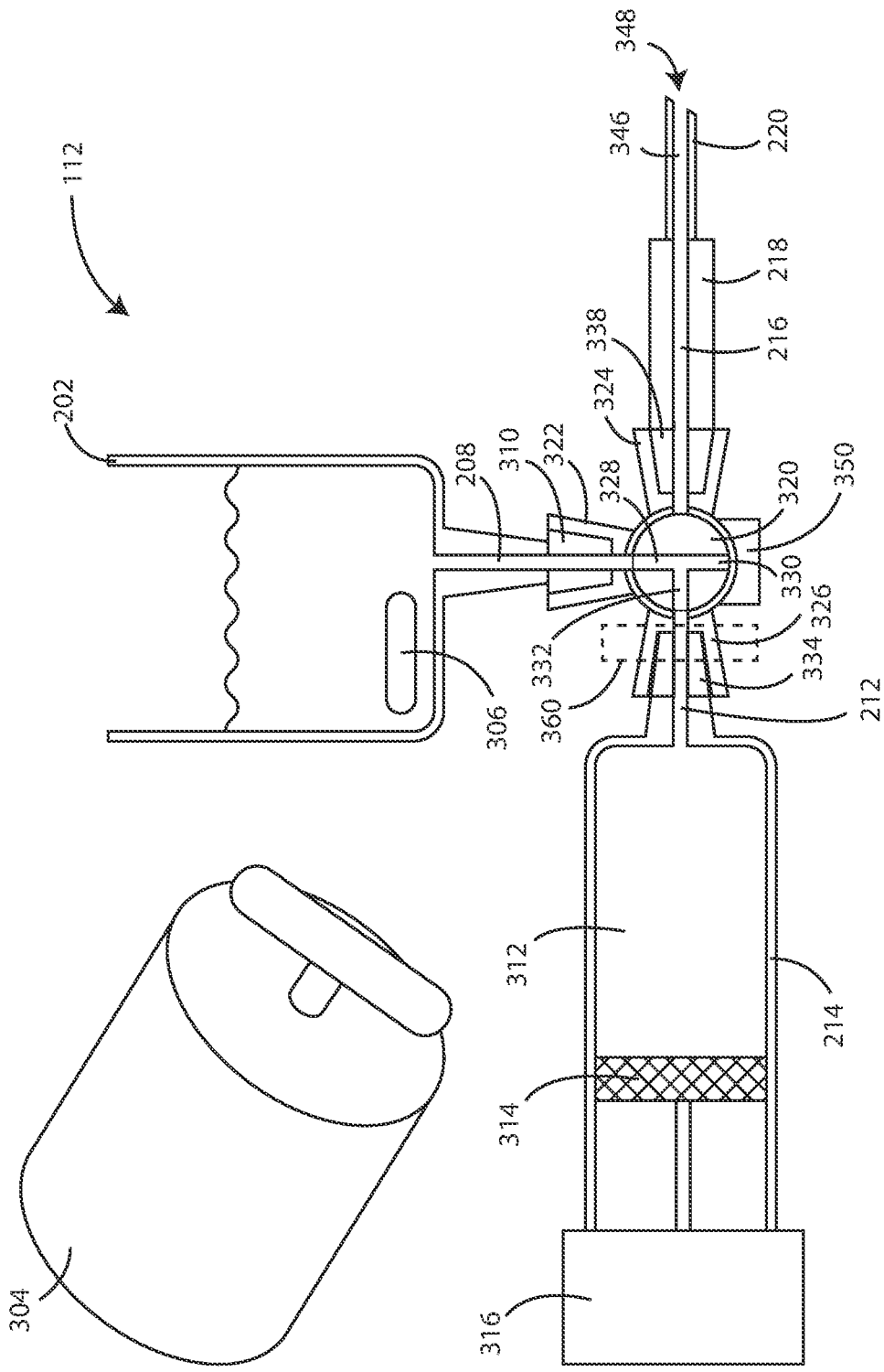
FIG. 3 is a schematic view of a coating application unit in accordance with various embodiments herein.

Referring now to FIG. 3, a schematic view of a coating application unit 112 is shown in accordance with various embodiments herein. The coating application unit 112 includes a fluid supply reservoir 202. The coating application unit 112 also includes a fluid supply conduit 208. The coating application unit 112 also includes a pump conduit 212. The coating application unit 112 also includes a reciprocating positive displacement pump 214. The coating application unit 112 also includes an applicator conduit 216. The coating application unit 112 also includes a fluid applicator 218.

An agitation unit can take the form of a rotating magnetic driver 304. The fluid supply reservoir 202 can include a magnetic stir bar 306 disposed therein. Movement of the rotating magnetic driver 304 can cause movement of the magnetic stir bar 306, thus providing agitation to the coating suspension within the fluid supply reservoir 202.

In this example, the valve takes the form of a three-way valve 320. The three-way valve 320 can include a first receiver 322, a second receiver 324, and a third receiver 326. The fluid supply reservoir 202 can includes a supply reservoir connection plug 310 that can fit into the first receiver 322. The reciprocating positive displacement pump 214 can include includes a pump connection plug 334 that can fit within the second receiver 324. The fluid applicator 218 can include an applicator connection plug 338 that can fit within the third receiver 326.

The three-way valve 320 can define a first path 328, a second path 332, and a third path 330. In various embodiments, the three-way valve 320 can be configured to assume a first fluid transport state and a second fluid transport state. In various embodiments, the three-way valve 320 provides fluid communication between the fluid supply reservoir 202 and the reciprocating positive displacement pump 214 when it is in the first fluid transport state utilizing the first path 328 and the second path 332. This first fluid transport rate can be used for filling and/or draining of the reciprocating positive displacement pump 214. In various embodiments, the three-way valve 320 also provides fluid communication between the reciprocating positive displacement pump 214 and the fluid applicator 218 when it is in the second fluid transport state utilizing the first path 328 and third path 330. The second fluid transport state can be used for applying a coating suspension to a medical device surface.

The reciprocating positive displacement pump 214 includes an interior volume 312. The reciprocating positive displacement pump 214 also includes a plunger 314. The reciprocating positive displacement pump 214 also includes a plunger actuator 316. The fluid applicator 218 includes an applicator tip 220. The applicator tip 220 includes a tip lumen 346. The applicator tip 220 also includes an orifice 348 out of which the coating suspension can flow as it is being applied to a surface of a medical device.

Figure 5:
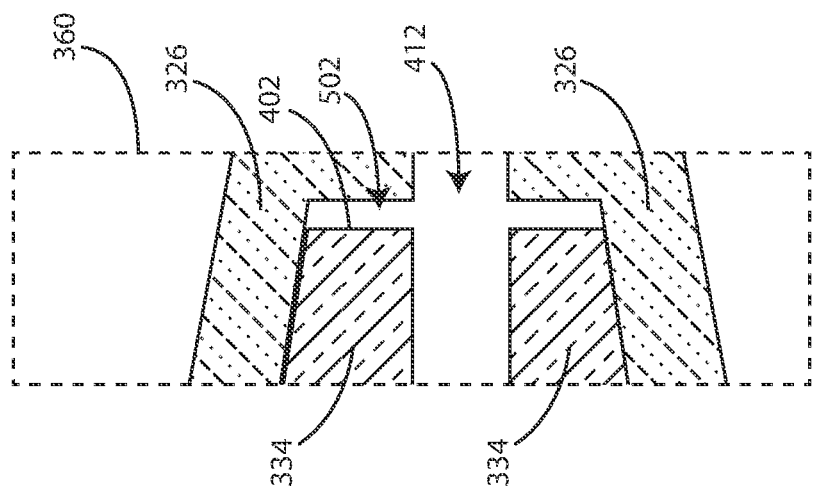
FIG. 5 is an enlarged schematic view of a portion of the coating application unit shown in FIG. 3 in accordance with various embodiments herein.

The coating application unit 112 also includes a portion 360 that will be described in greater detail below with respect to FIGS. 4 and 5. While not intending to be bound by theory, it has been found that expansions in the cross-sectional area of the fluid flow path can be detrimental to the stability of the suspension and can lead to clumping and other sorts of suspension failures. As such, in various embodiments herein, the fluid flow path is configured to reduce or eliminate points where its cross-sectional area expands. In various embodiments herein, the fluid flow path is configured to reduce or eliminate cavities.

Figure 4:
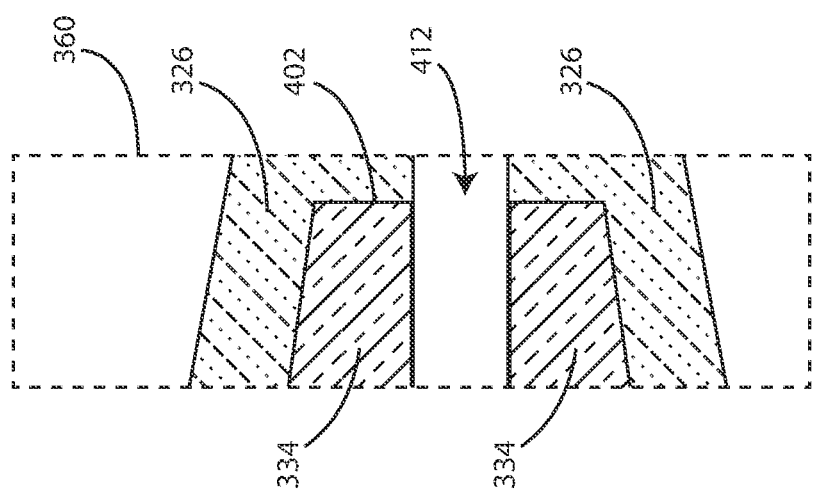
FIG. 4 is an enlarged schematic view of a portion of the coating application unit shown in FIG. 3 in accordance with various embodiments herein.

Referring now to FIG. 4, an enlarged schematic view of a portion 360 of the coating application unit 112 of FIG. 3 is shown in accordance with various embodiments herein. In this view, the third receiver 326 has the pump connection plug 334 inserted therein. The plug tip 402 is positioned to the very end of the third receiver 326. Thus, the fluid flow path 412 is substantially continuous and does not include a cavity (or dead space). FIG. 5 serves to show the scenario when the pump connection plug 334 does not fit properly in the third receiver 326 and/or does not take up the full space within the third receiver 326. Referring now to FIG. 5, an enlarged schematic view of a portion 360 of the coating application unit 112 of FIG. 3 is shown in accordance with various embodiments herein. The plug tip 402 does not extend to the end of the interior of the third receiver 326. Thus, FIG. 5 shows a cavity 502. While not intending to be bound by theory, such cavities can be detrimental to consistent coating processes. The rapid expansion in cross-sectional area of the flow path can cause the suspension to clump amongst other detrimental effects.

Figure 6:
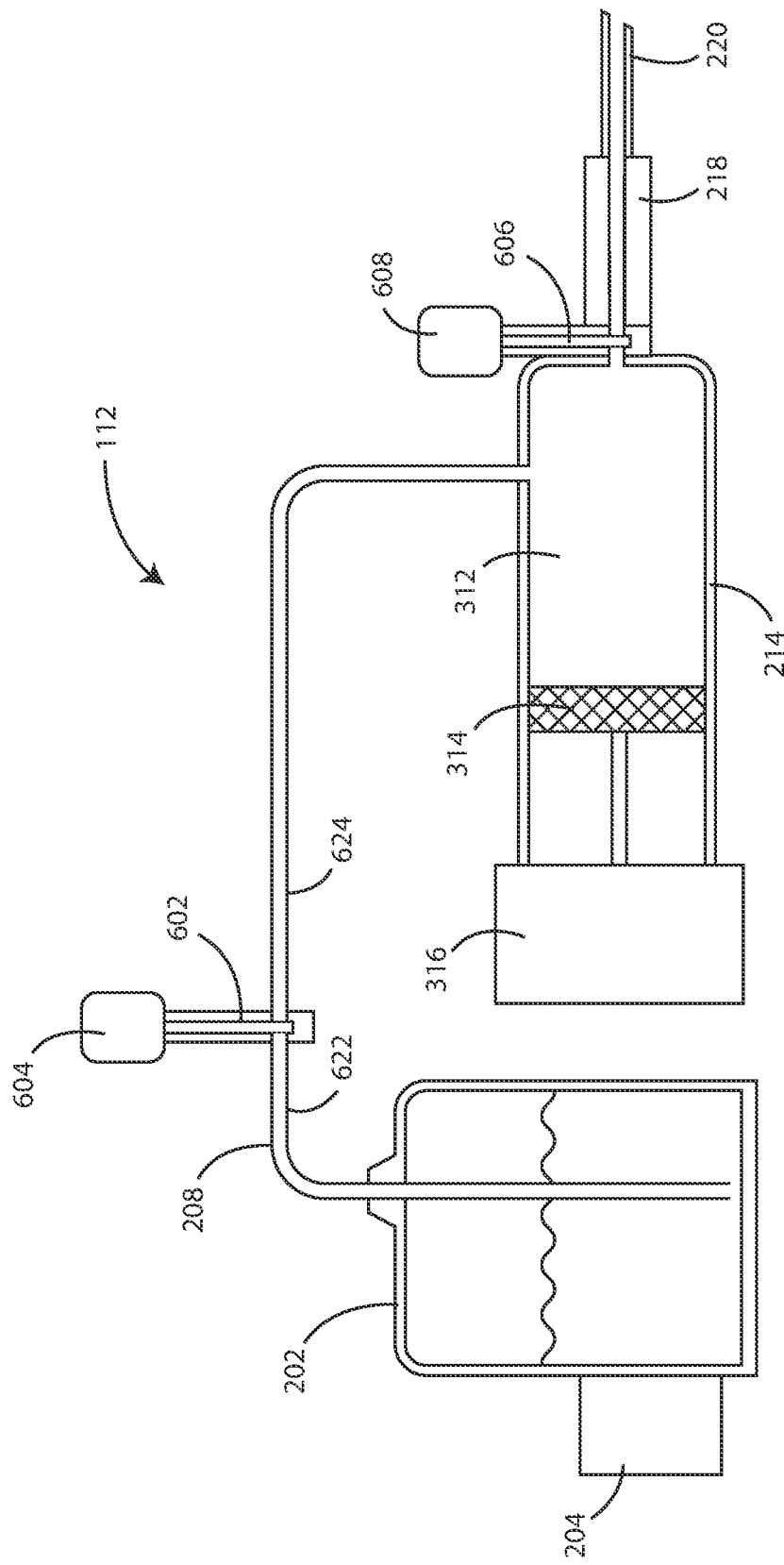
FIG. 6 is a schematic view of a coating application unit is shown in accordance with various embodiments herein.

Referring now to FIG. 6, a schematic view of a coating application unit 112 is shown in accordance with various embodiments herein. The coating application unit 112 includes a fluid supply reservoir 202. The fluid supply reservoir 202 can include a coating suspension disposed therein. In various embodiments, the coating application unit 112 can function to apply the coating suspension to a medical device surface (exemplary medical devices are described in greater detail below). The coating application unit 112 also includes an agitation unit 204. The agitation unit 204 can serve to provide stirring or agitation to a coating suspension within the fluid supply reservoir 202. In some embodiments, the agitation unit 204 includes an electric motor and/or solenoid. In some embodiments, the agitation unit 204 can drive a stirring bar or paddle either directly (e.g., a direct mechanical connection) or indirectly (such as with a magnetic force). In some embodiments, the agitation unit 204 can include a source of vibration and/or sonic or ultrasonic energy.

The coating application unit 112 also includes a fluid supply conduit 208. The coating application unit 112 also includes a first valve 602 and first valve actuator 604. The first valve 602 can serve to divide or interrupt the fluid supply conduit 208 into a supply side 622 and a pump side 624. As such, in some embodiments, the first valve 602 can serve to selectively isolate the pump 214 from the fluid supply reservoir 202 in terms of both fluid flow and in terms of movement/vibration that may result from the action of the agitation unit 204. While not intending to be bound by theory, this isolation can be useful to prevent movement/vibration from being transmitted to other parts of the apparatus, such as the fluid applicator 218 and/or the applicator tip 220.

The first valve 602 can include many different types of valves. In some embodiments, the first valve 602 is a type of valve with little or no dead space. In some embodiments, the first valve 602 is a needle valve, a diaphragm valve, a ball valve, or a gate valve, or a knife gate valve. In some embodiments, the first valve 602 can also be a butterfly valve, a globe valve, parallel slide valve, a pinch valve, a piston valve, a plug valve, or a sluice valve. In some embodiments, first valve actuator 604 can include a pneumatic actuator (diaphragm, piston, etc.), a hydraulic actuator, an electric actuator (solenoid, stepper motor, etc.), or the like.

In this embodiment, the coating application unit 112 also includes a reciprocating positive displacement pump 214. However, it will be appreciated that the pump can take on various different forms. In some embodiments, the pump or reciprocating positive displacement pump is selected from the group consisting of a plunger pump, a piston pump, a diaphragm pump, and a syringe pump. In some embodiments, a reciprocating positive displacement pump can specifically be a single-acting reciprocating pump. In some embodiments, the pump can specifically be a syringe pump.

The reciprocating positive displacement pump 214, can include an interior volume 312, plunger 314, and plunger actuator 316. The pump side 624 of the fluid supply conduit 208 is in fluid communication with the interior volume 312 of the reciprocating positive displacement pump 214.

The coating application unit 112 also includes a second valve 606 and second valve actuator 608. The second valve 606 can be the same type of valve as the first valve 602 (examples described above) or can be different from the first valve 602. The coating application unit 112 also includes a fluid applicator 218 which can include an applicator tip 220. The second valve 606 is positioned between the pump 214 and the applicator tip 220. In operation, during a filling step, the first valve 602 opens and the second valve 606 closes. The interior volume 312 can be filled with a coating fluid, such as by withdrawing the plunger 314. The, during a coating application step, the first valve 602 closes and the second valve 606 opens. The coating fluid from the interior volume 312 can then be conveyed to the fluid applicator 218 and onto the applicator tip 220.

In various embodiments, the fluid supply reservoir 202 can be in fluid communication with the valve 210. In various embodiments, the valve 210 can be configured to assume a first fluid transport state and a second fluid transport state. In various embodiments, the valve 210 provides fluid communication between the fluid supply reservoir 202 and the reciprocating positive displacement pump 214 when it is in the first fluid transport state. This first fluid transport rate can be used for filling and/or draining of the reciprocating positive displacement pump 214. In various embodiments, the valve 210 also provides fluid communication between the reciprocating positive displacement pump 214 and the fluid applicator 218 when in the second fluid transport state. The second fluid transport state can be used for applying a coating suspension 206 to a medical device surface. The fluid applicator 218 can include an applicator tip 220.

As referenced above, the first valve 602 can serve to selectively isolate the pump 214 from the fluid supply reservoir 202 in terms of both fluid flow and in terms of movement/vibration that may result from the action of the agitation unit 204. This isolation can be useful to prevent movement/vibration from being transmitted to other parts of the apparatus, such as the fluid applicator 218 and/or the applicator tip 220 when the system is in the second fluid transport state or the coating application state. Thus, in various embodiments herein, vibration or other movement caused by the agitation unit 204 is prevented from reaching the fluid applicator 218 and/or the applicator tip 220 when the system is in the coating application state. In various embodiments, vibration or other movement caused by the agitation unit 204 is attenuated by at least 50% (such as 50% reduction in a measured peak amplitude) as measured at an applicator tip 220 of the fluid applicator 218 when the system is in the coating application state versus the filling state. In various embodiments, vibration or other movement caused by the agitation unit 204 is attenuated by at least 10, 20, 30, 40, 50, 60, 70, 80, 90, or 95% in peak amplitude.

Figure 7:
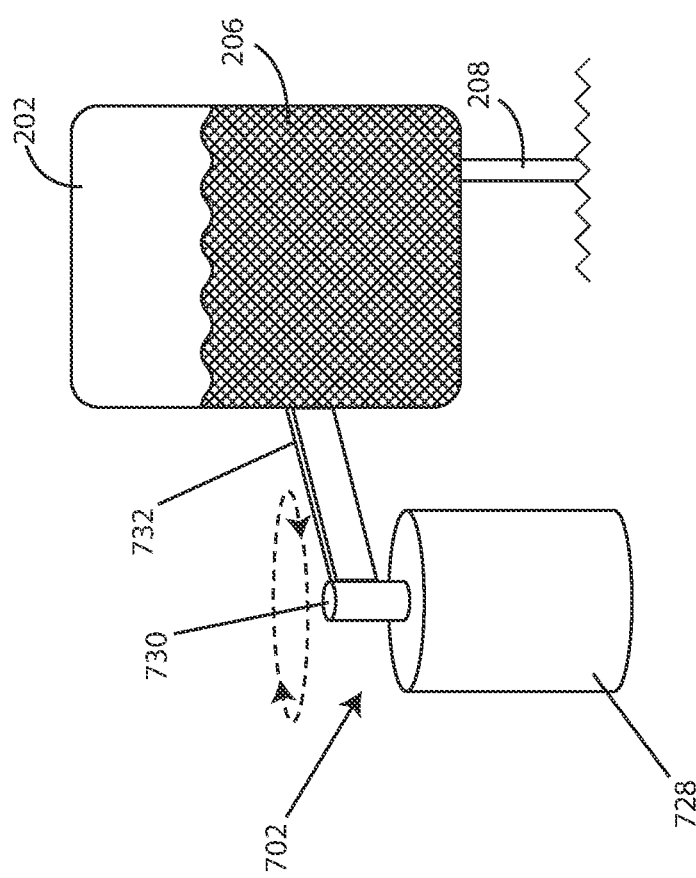
FIG. 7 is a schematic view of components of an apparatus for coating a medical device in accordance with various embodiments herein.

Referring now to FIG. 7, a schematic view is shown of components of an apparatus for coating a medical device in accordance with various embodiments herein. The apparatus includes an agitation unit in the form of a striking assembly 702, a fluid supply reservoir 202, a coating suspension 206 within the fluid supply reservoir 202, and a fluid supply conduit 208.

The striking assembly 702 can include various components. In some embodiments, the striking assembly 702 can include an electric motor 728 that drives a rotating shaft 730. The electric motor 728 can be of various types including, but not limited to, a stepper motor, AC or DC type motors, mechanically commutated, electronically commutated, externally commutated (including asynchronous and synchronous), and the like. A striking arm 732 can be connected to the rotating shaft 730. The striking arm 732 can be rotated by the electric motor 728 by virtue of being connected to the rotating shaft 730. The fluid supply reservoir 202, or a portion thereof, can be located close enough to the striking arm 732 such that the striking arm 732 strikes the fluid supply reservoir 202, or a portion thereof, as the striking arm 732 rotates.

The fluid supply reservoir 202 can be of various sizes. In some embodiments, the fluid supply reservoir 202 can have an interior volume of between about 1 mL to about 2000 mL. In some embodiments, the fluid supply reservoir 202 can have an interior volume of between about 10 mL to about 500 mL The fluid supply reservoir 202 can be formed of various materials, including but not limited to, polymer, metal, glass, composite and the like.

The striking arm 732 (or a component attached to the striking arm) can be configured to contact the supply reservoir container of another portion of the fluid supply reservoir 202 at a height that is less than the height of an active agent suspension within the fluid supply reservoir 202 (e.g., below the upper surface). In some embodiments, an actuator can be used to change the height of the fluid supply reservoir 202, the striking arm 732, or a component connected to the striking arm 732, or both in order to change the relative position of wherein the striking arm 732 or an element connected thereto, impacts the fluid supply reservoir 202 (directly or indirectly). However, in other embodiments, the vertical positions of the components are fixed with respect to one another. In some embodiments, the striking arm 732 (or a component attached to the striking arm) can be configured to contact the fluid supply reservoir 202 of another portion of the fluid supply reservoir 202 at a height that is greater than the height of the active agent suspension within the fluid supply reservoir 202 (e.g., below the upper surface).

In some embodiments, an apparatus herein can also include a control module. The control module can include a controller circuit and can be in electrical communication with various other elements of the apparatus such as the striking assembly 702 and other components of the system in order to control aspects of their operation. The control module can be implemented using any suitable technology, and may include, for example, a printed circuit board (PCB) with one or more microchips, such as a microcontroller, a programmable logic controller (PLC), an ASIC, an FPGA, a microprocessor, or other suitable technology.

The control module can control operations of the striking assembly 702. For example, the control module can turn the electric motor 728 off and on and control aspects of its operation such as the rotation speed, whether rotation is continuous or discontinuous, or the like. The rotating shaft 730 can be rotated at various speeds. In some embodiments, the rotating shaft 730 is rotated at a speed of between 0.5 RPM and 30 RPM. In some embodiments, the striking arm 732 is rotated at a speed of between 0.5 RPM and 30 RPM. In various embodiments, the rotating shaft and/or the striking arm can be rotated at speeds of 0.5, 1, 2, 3, 4, 5, 6, 7, 8, 9, 10, 15, 20, 25, or 30 RPM. In various embodiments, the rotating shaft and/or the striking arm can be rotated at speeds in a range wherein any of the preceding RPM values can serve as the upper or lower bounds of the range, provided that the upper bound is faster than the lower bound. In various embodiments, striking the supply reservoir occurs at a frequency of about 0.5 to about 30 Hertz. In some embodiments, striking the supply reservoir occurs at a frequency of about 2 to about 8 Hertz. In some embodiments, striking the supply reservoir occurs at a frequency of about 4 to about 6 Hertz.

Referring now to FIG. 8, a schematic top view is shown of a striking assembly 702 and a fluid supply reservoir 202 in accordance with various embodiments herein. In this view, the striking assembly 702 includes an electric motor 728, a rotating shaft 730 and a striking arm 732 connected to the rotating shaft 730. In this view, a bumper 802 is shown attached the rotating shaft 730. The bumper 802 can function to focus the point of impact between the striking assembly 702 and the fluid supply reservoir 202. However, in some embodiments, a bumper is not included. The bumper 802 can take on various shapes including a domed shape, pyramidal, frustoconical, raised square, raised polygon, and the like. The bumper 802 can be formed of various materials including metal, polymer, ceramic, glass, composite, and the like.

The electric motor 728 causes the rotating shaft 730, striking arm 732 and bumper 802 to rotate and strike the fluid supply reservoir 202, or a portion thereof. The force of the striking assembly 702 can cause the fluid supply reservoir 202, or a portion thereof, to move in the direction of arrow 804. In some embodiments, the force of the striking assembly 702 can cause formation of shock wave that passes through the suspension. However, in various embodiments, the force of the striking assembly 702 is not so great that it causes the suspension to splatter on the opposite interior wall of the fluid supply reservoir 202.

In FIG. 8, the fluid supply reservoir 202 is shown having a circular outside profile. However, it will be appreciated that the fluid supply reservoir 202 can take on many different shapes. By way of example, the supply reservoir container can be ovoid, polygonal, square, and the like.

While the striking assembly 702 is shown spinning in a clockwise direction, it will be appreciated that the striking assembly 702 can also spin in a counter-clockwise direction. In some embodiments, the striking assembly 702 can spin continuously. In other embodiments, the striking assembly 702 can spin intermittently.

In some embodiments, the supply reservoir assembly can include a frame or frame member. Referring now to FIG. 9, a schematic top view is shown of a striking assembly and a supply reservoir assembly in accordance with various embodiments herein. The frame member 904 can serve to hold and/or support other components of a supply reservoir assembly such as the fluid supply reservoir 202 itself. The frame member 904 can also serve to mount the fluid supply reservoir 202 in a desired position. The frame member 904 can also be configured to allow for movement of the fluid supply reservoir 202 such as allowing the supply reservoir to move laterally in a swinging or sliding type motion.

In some embodiments, the frame member 904 can be connected to a pivoting joint 906. The pivoting joint 906 forms a pivot point about which at least a portion of the frame swings laterally. In some cases, the pivot point is located at the top-most portion of the frame. However, other positions are also contemplated herein.

In some embodiments, the frame member 904 can be connected to a center pin or shaft 908. The shaft 908 can fit within a channel 910 defined by a mounting structure 902 and be supported by bushings, bearings, or non-supported by such elements. The shaft 908 can spin within the channel 910. This can cause the portion of the frame member 904 holding the fluid supply reservoir 202 to swing laterally away from the striking arm 732 and bumper 802 after the bumper 802 makes contact with the frame member 904 or the fluid supply reservoir 202. It will be appreciated, however, that there are many different ways of allowing the supply reservoir to move laterally (either swinging or sliding). In various embodiments, the apparatus can include a spring or a structure that can provide a spring force so that the frame member 904 or the fluid supply reservoir 202 itself is biased into a particular position, such as a position closest to the place where the striking arm 732 contacts the fluid supply reservoir 202.

Figure 10:
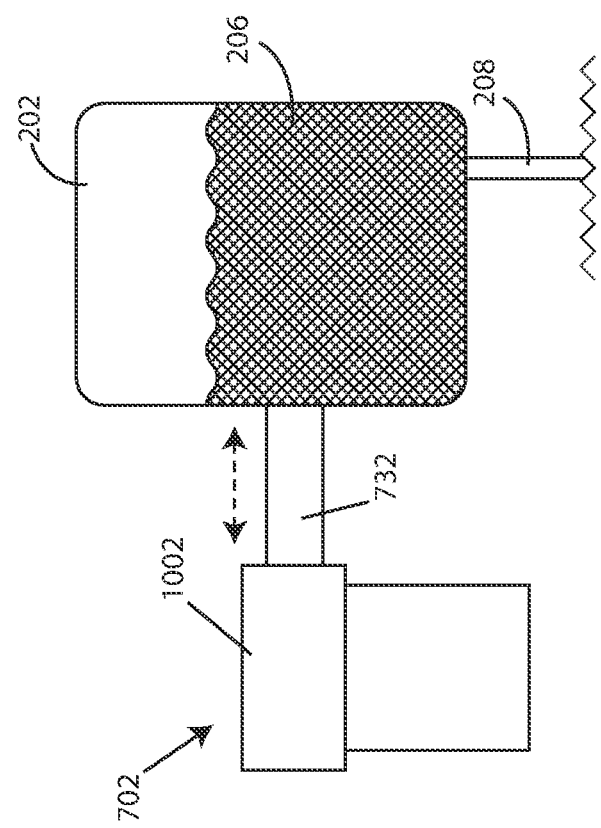
FIG. 10 is a schematic view of an apparatus for coating a medical device in accordance with various embodiments herein.

In many embodiments, the striking arm spins and contacts the supply reservoir assembly at a particular point or area during each revolution or cycle. However, many other types of striking mechanism are contemplated herein. By way of example, striking mechanisms that move linearly, or substantially linearly, can also be used instead of, or in addition to, those that spin or rotate. Referring now to FIG. 10, a schematic view is shown of components of an apparatus for coating a medical device in accordance with various embodiments herein. The apparatus includes a striking assembly 702 and a fluid supply reservoir 202. In this embodiment, the striking assembly 702 includes a linear actuator 1002 that causes a striking arm 732 to move substantially linearly and strike or impact the fluid supply reservoir 202, or a portion thereof.

Figure 11:
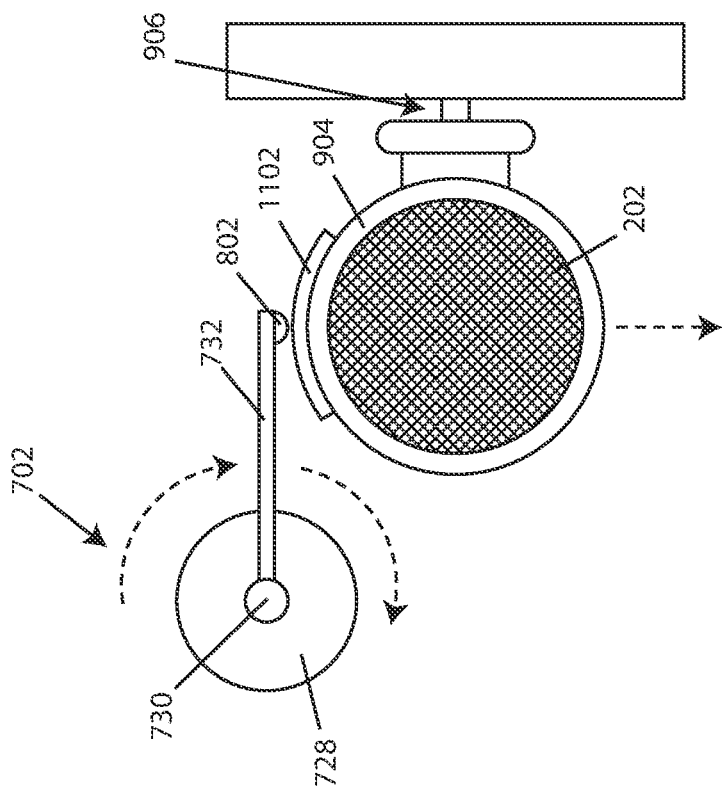
FIG. 11 is a schematic top view of a striking assembly and a fluid supply reservoir in accordance with various embodiments herein.

It will be appreciated that various other components and/or structures can be included in embodiments herein. In some embodiments, a shield or striking pad can be included on the frame member or the supply reservoir and can be positioned in the area where the striking member contacts the supply reservoir assembly. Referring now to FIG. 11, a schematic top view is shown of a striking assembly 702 and a fluid supply reservoir 202 in accordance with various embodiments herein. A frame member 904 can be included and can serve to hold and/or support other components of the fluid supply reservoir 202 such as the fluid supply reservoir 202 itself. The frame member 904 can be connected to a pivoting joint 906. A striking pad 1102 can be connected to the frame member 904 and can be positioned in the area where the striking assembly strikes or contacts the supply reservoir assembly. The striking pad 1102 can be formed of various materials, including but not limited to, polymer, metal, glass, composite, or the like.

Figure 12:
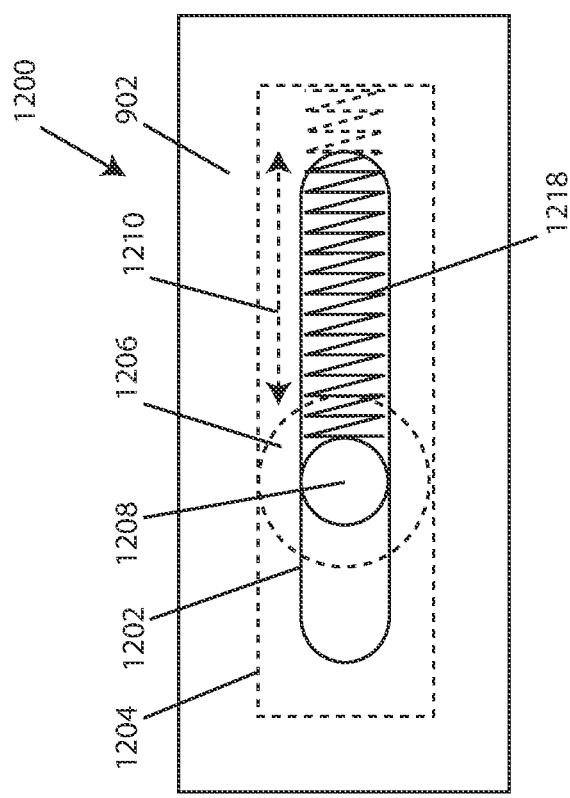
FIG. 12 is a schematic side view of a sliding mechanism in accordance with various embodiments herein.

In many embodiments, the apparatus can be configured to allow the supply reservoir to swing laterally. However, in various embodiments, the apparatus can also be configured to allow the supply reservoir to slide laterally, in addition to or instead of swinging laterally. Referring now to FIG. 12, a schematic side view is shown of a sliding mechanism 1200 in accordance with various embodiments herein. The sliding mechanism 1200 can include an interior channel 1204, defined by mounting structure 902 (or a similar structure), in which an interior member 1206 can slide or roll back and forth in the direction of arrow 1210. The interior member 1206 can be biased into a particular position through force applied by spring 1218 or another similar structure. The interior member 1206 can be connected to shaft 1208 which can move back and forth within window 1202. Window 1202 can have smaller dimensions than interior member 1206, thus keeping interior member 1206 confined to within interior channel 1204. It will be appreciated, however, that many different sliding and/or swinging joints are contemplated herein.

Figure 13:
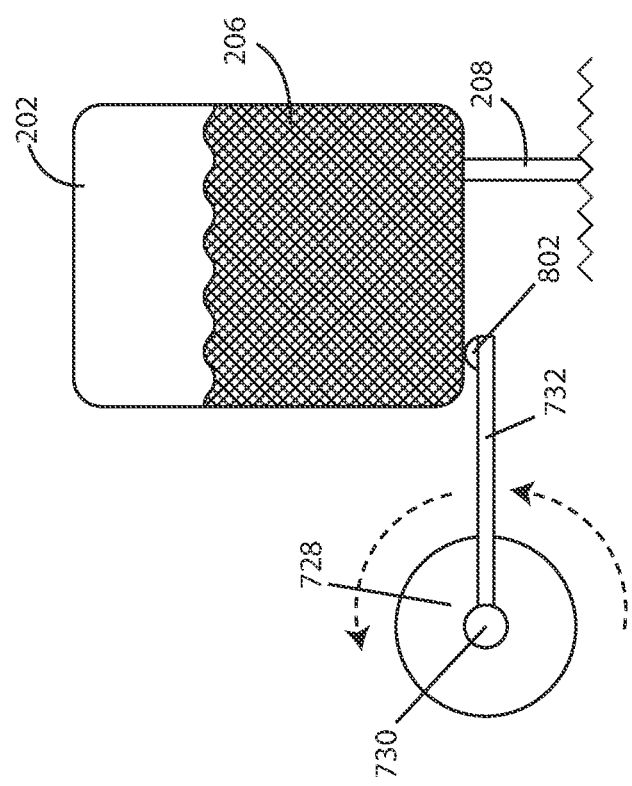
FIG. 13 is a schematic view of components of an apparatus for coating a medical device in accordance with various embodiments herein.

While many of the foregoing illustrations have depicted the striking assembly contacting the supply reservoir or supply reservoir assembly from the side, it is also expressly contemplated herein that the striking assembly can also contact the supply reservoir assembly from the bottom or the top. By way of example, referring now to FIG. 13, a schematic view is shown of components of an apparatus for coating a medical device in accordance with various embodiments herein. The apparatus includes a striking assembly 702 and a fluid supply reservoir 202. In this embodiment, the striking assembly 702 is configured so that the striking arm 732 and bumper 802 contact the bottom of the fluid supply reservoir 202.

Medical Devices

It will be appreciated that many different medical devices can be coated using equipment and methods herein. In various embodiments, rotatable medical device can be coated using equipment and methods described herein. In various embodiments, relatively long medical devices (such as those having a length that it is at least 20 times their diameter) can be coated using equipment and methods described herein.

One type of medical device is a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guide wire, and manifold. A balloon catheter generally includes an elongated catheter shaft with an inflatable balloon attached to a distal section of the catheter shaft. At a proximal end of the catheter shaft, there is typically a manifold. At the manifold end, placement of the catheter can be facilitated using a guide wire. Guide wires are small and maneuverable when inserted into an artery. Once the guide wire is moved to the target location, the catheter with balloon portion is then fed over the guide wire until the balloon reaches the target location in the vessel. The balloon is typically inserted into the arterial lumen of a patient and advanced through the lumen in an unexpanded state. The balloon is then inflated when the catheter reaches target site resulting in application of mechanical force sufficient to cause vessel dilation. The balloon is typically inflated using a fluid, which is injected through an inflation port. The manifold can control the fluid introduction within shaft for expansion of the balloon. The mechanics of fluid transfer and introduction within balloons vary according to the specific design of the catheter, and are well known in the art.

Figure 14:
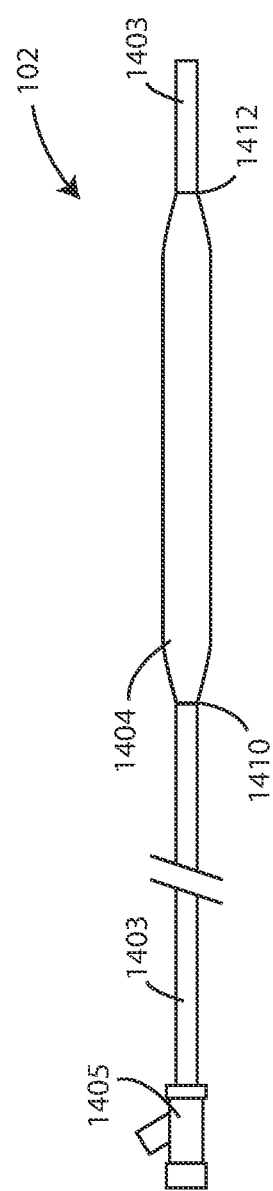
FIG. 14 is a schematic view of a medical device in accordance with various embodiments herein.

Referring now to FIG. 14, a schematic view of a medical device 102 is shown. The medical device 102 can optionally include a connection manifold 1405, a shaft 1403 having a surface, and an expandable portion 1404 (such as a balloon) having a surface. The expandable portion 1404 can include a proximal end 1410 and a distal end 1412. Coating segments can be disposed onto one or more of the shaft 1403 and the expandable portion 1404. In some embodiments, the expandable portion 1404 can include multiple coating segments thereon disposed adjacently to one another.

Coating Compositions

It will be appreciated that coating compositions applied onto medical devices herein as a fluid can include various components including, but not limited to, one or more active agents, carrier agents and/or solvents, polymers (including degradable or non-degradable polymers), cross-linking agents, excipients, and the like. The relative amounts of the components of the coating composition will depend on various factors including the desired amount of active agent to be applied to the balloon and the desired release rate of the active agent. Exemplary coating compositions are described in U.S. Publ. Pat. Appl. No. 2018/0110903, the content of which is herein incorporated by reference. Exemplary cross-linking agents are described in U.S. Pat. No. 8,889,760, the content of which is herein incorporated by reference. In some embodiments, active agents can specifically include those wherein the coating composition is the form of a suspension or emulsion including active agent particles.

In some particular embodiments, the coating suspension can include a suspension of active agent particles within a liquid carrier. In some particular embodiments, the coating suspension can include a suspension of active agent particles within a liquid carrier along with one or more other agents. In some particular embodiments, the coating suspension can include a suspension of active agent particles within a liquid carrier along with a cationic agent. In an embodiment, the coating suspension can include sirolimus, polyethyleneimine (PEI), and water.

In an embodiment, the weight ratio of sirolimus to PEI is from 1:99 to 99:1, or 50:50 to 99:1, or 80:20 to 99:1, or, 90:10 to 99:1, or 95:5 to 99:1. In an embodiment, the concentration of sirolimus is about 25 mg/ml, 50 mg/ml, 75 mg/ml, 100 mg/ml, 125 mg/ml, 150 mg/ml, 200 mg/ml, 300 mg/ml, 400 mg/ml, 500 mg/ml, or 750 mg/ml, or a concentration falling within a range between any of the foregoing.

In an embodiment, the coating suspension can have a viscosity of about 1 to 500, 5 to 100, 5 to 50, 5 to 30, or 8 to 10 centipoise at a shear rate of 300 [1/s].

In some embodiments, the coating suspension or composition can include a crystalline active agent. In some embodiments, the composition can include a semi-crystalline or amorphous active agent. In various embodiments, the active agent can be in a solid (undissolved form).

In various embodiments, the composition can be a suspension including an active agent particulate. However, in some embodiments, the composition can also include emulsions, dispersions and the like. Also, in some embodiments, the composition can include true solutions.

Active agents herein can include hydrophobic active agents, hydrophilic active agents, or a combination of both. In various embodiments, the active agent composition includes one or more hydrophobic active agents. In general, the term "hydrophobic active agent" refers to an active agent having solubility in water of less than about 100 µg/mL at 25° C. and neutral pH, less than about 10 µg/mL at 25° C. and neutral pH, or less than about 5 µg/ml at 25° C. and neutral pH. In various embodiments, the hydrophobic active agent is crystalline. In general, the term "crystalline" refers to a thermodynamically stable solid form of an active agent having "long range molecular order" in which the molecules are packed in a regularly ordered, repeating pattern. In another embodiment, the hydrophobic active agent is amorphous. The term "amorphous" refers to a solid form of an active agent in which the molecules do not have "long range molecular order", but rather are randomly arranged or retain only a "short range molecular order" typical of liquids.

The amount of active agent included in the active agent composition can vary depending upon many factors including the desired therapeutic outcome. However, compositions herein generally include at least about 1 mg/ml, 2 mg/ml, 3 mg/ml, 4 mg/ml, 5 mg/ml, or 10 mg/ml, 15 mg/ml, 20 mg/ml, or 25 mg/ml or up to about 25 mg/ml, 50 mg/ml, 75 mg/ml, 100 mg/ml, 125 mg/ml, 150 mg/ml, 175 mg/ml, 200 mg/ml, 225 mg/ml, 250 mg/ml, 275 mg/ml, 300 mg/ml, or even 325 mg/ml active agent.

It will be appreciated that hydrophobic active agents can include agents having many different types of activities. In some embodiments, hydrophobic active agents can include, but are not limited to, antiproliferatives such as paclitaxel and analogues thereof, sirolimus (rapamycin), everolimus, biolimus A9, zotarolimus, tacrolimus, pimecrolimus and other sirolimus derivatives, and mixtures thereof; analgesics and anti-inflammatory agents such as aloxiprin, auranofin, azapropazone, benorylate, diflunisal, etodolac, fenbufen, fenoprofen calcium, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecainide acetate, quinidine sulphate; anti-bacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexol HCl, biperiden, ethopropazine HCl, hyoscyamine, mepenzolate bromide, oxyphencylcimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as amrinone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate.

Other hydrophobic active agents include, but are not limited to, active agents for treatment of hypertension (HTN), such as guanethidine.

In a particular embodiment, the hydrophobic active agent includes paclitaxel, sirolimus (rapamycin), everolimus, biolimus A9, zotarolimus, tacrolimus, and pimecrolimus and mixtures thereof.

In some embodiments, the hydrophobic active agent includes chemotherapeutics, exemplified by the family of fluorouracils (e.g. 4-FU and 5-FU) and carmustine (BCNU 1,3-bis (2-chloroethyl)-1-nitrosourea) and temozolomide.

In various embodiments, the hydrophobic active agent is combined with a cationic delivery agent in solution. In various embodiments, the hydrophobic active agent is combined with a cationic delivery agent to form a suspension. In another embodiment, solid hydrophobic active agent, amorphous or crystalline, is combined with pure or neat cationic delivery agent, amorphous or crystalline, to form a mixture. In other embodiments, the hydrophobic active agents is conjugated to a cationic delivery agent. The conjugation can include a hydrophobic active agent covalently bonded to the cationic delivery agent. In some embodiments wherein the hydrophobic agent is conjugated to the cationic delivery agent a linking agent can be used to attach the hydrophobic agent to the cationic delivery agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

In various embodiments the active agent can be part of a microparticle. The term "microparticle" as used herein shall refer to non-dissolved particulate matter. In some embodiments, microparticles can include a polymer. In some embodiments, the microparticle can include a polymer that is distinct from the other polymers that may be used. Including a polymer within the microparticle can offer the advantage of providing additional control over the elution rate of the active agent. In some embodiments, including a polymer within the microparticle can also offer the advantage of increased protection of active agent activity.

Both hydrophobic and hydrophilic polymers can be used in embodiments of the invention. Both degradable and non-degradable polymers can be used in embodiments of the invention. The use of degradable polymers in the elution control coating can offer the advantage of controlling elution rate of an active agent without depending solely on the process of the active agent diffusing through the matrix itself. Rather, as the matrix erodes (through bulk or surface erosion) the active agent is released into the local environment of the elution control coating. The term "degradable" as used herein with reference to polymers, shall refer to those natural or synthetic polymers that break down under physiological conditions into constituent components over a period of time. By way of example, many degradable polymers include hydrolytically unstable linkages in the polymeric backbone. The cleavage of these unstable linkages leads to degradation of the polymer. The terms "erodible", "bioerodible", "biodegradable" and "non-durable" shall be used herein interchangeably with the term "degradable".

The polymer used with the microparticle can be degradable or non-degradable. A specific polymer can be selected based on various factors including compatibility with the active agent, whether or not the polymer is degradable, speed and habit of erosion (bulk or surface), and compatibility or incompatibility with solvents used to apply the coating.

In an embodiment, the microparticle includes a degradable polymer. Elution of an active agent from a particle including a degradable polymer can be from diffusion of the active agent through the degradable polymer itself or through the erosion (bulk or surface erosion) of the degradable polymer. Degradable polymers can include those described in more detail below.

Microparticles used with embodiments of the invention may be configured to provide a desired active agent elution rate. The rate of active agent elution from a microparticle will depend on various factors including the size of the microparticle, the presence or absence of other components in the microparticle such as a polymer, an additive, or a solvent, the erosion characteristics of the material in the microparticle, the structural features of the microparticle including porosity, overcoats and the like. By way of example, microparticles with a larger diameter may elute an active agent more slowly than microparticles of a smaller diameter. In addition, microparticles with too large of a diameter may result in a coating with a rough surface and may clog coating equipment. In some embodiments, microparticles used with embodiments of the invention have an average size distribution in the range between about 10 nm to about 100 μm as measured by SEM analysis. In an embodiment, microparticles are equal to or less than about 5 μm.

In some embodiments, the microparticles used are substantially monodisperse. In other embodiments, the microparticles used are polydisperse. In some applications, the use of monodisperse microparticles is advantageous because elution rates from monodisperse microparticles can be more consistent than release rates from otherwise similar polydisperse microparticles.

Microparticles having a characteristic elution rate can be combined with other microparticles having the same or a different characteristic elution rate. By combining particles with different characteristic release rates, the overall release rate of an active agent from the particles and from the matrix that the particles are dispersed in can be manipulated as desired. For example, microparticles having a relatively fast elution rate can be combined in a coating with microparticles having a relatively slow elution rate to produce a composition elution profile that is desirable.

In some embodiments, various additives can be used to enhance the stability of the suspension of microparticles. Additives may include various components such as surfactants, stabilizers, etc. In some embodiments, a polymer is used to enhance the stability of the suspension of microparticles. By way of example, addition of a (poly(butyleneterephthalate-co-ethylene glycol) copolymer can enhance the stability of the suspension.

In some embodiments, particulates herein are formed by preparing a drug-containing particle (e.g., a core particle) along with biocompatible polymer that has negatively charged groups or that can be treated to provide negatively charged groups, and then associating a cationic agent with the negatively charged groups of the particulate to provide the particulate with a positive zeta-potential. Drug-containing particulates that can be used in the embodiments as described herein are detailed in the provisional application Ser. 62/315,917 entitled "Drug-Containing Particulate Composition with Cationic Agent, Associated Medical Devices, and Methods for Treatment" to Slager; filed Mar. 31, 2016, the entire application of which is incorporated herein by reference.

In one aspect (e.g., a first particle aspect of the disclosure), the bioactive agent particulates include a core particle having a bioactive agent and a first biocompatible polymer. There is a layer around the core particle that includes a second biocompatible polymer which includes negatively charged groups. The second biocompatible polymer is chosen to be more water soluble than the first biocompatible polymer. A cationic agent is associated with the negatively charged groups of particulate in a manner that provides the particulate with a positive zeta-potential. "Biocompatible" polymers are those that do not provoke any significant adverse effects when introduced into the body.

In a mode of practice, the particles of the first particle aspect of the disclosure can be prepared by first preparing a first composition that includes the bioactive agent and first biocompatible polymer. Next, the first composition is contacted with a composition that includes the second biocompatible polymer having negatively charged groups. This forms an intermediate particle with negatively charged groups on the outer surface, and a core particle including the bioactive agent and first biocompatible polymer. Next, the intermediate particle is contacted with a composition that include cationic agent so that the resulting particulate has a positive zeta-potential.

The first biocompatible polymer can be an organic solvent-soluble degradable polymer. Examples of degradable polymers can include those with hydrolytically unstable linkages in the polymeric backbone. The degradable polymers can exhibit bulk erosion or surface erosion characteristics. Synthetic degradable polymers can include: degradable polyesters (such as poly(glycolic acid), poly(lactic acid), poly(lactic-co-glycolic acid), poly(dioxanone), polylactones (e.g., poly(caprolactone)), poly(3-hydroxybutyrate), poly(3-hydroxyvalerate), poly(valerolactone), poly(tartronic acid), poly(β-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; and degradable polyhydroxyalkanoates; and copolymers thereof.

In some aspects the second polymer is a biodegradable block copolymer comprising hydrophilic and hydrophobic blocks. The linkages between the blocks can be biodegradable or biostable, and the hydrophilic and hydrophobic blocks can be either or both biodegradable or biostable, with at least one portion of the copolymer being biodegradable.

In some aspects the hydrophobic blocks include a biodegradable polymeric segment selected from polycaprolactone (PCL), polyvalerolactone (PVL), poly(lactide-co-glycolide) (PLGA), polylactic acid (PLA), polybutyrolactone (PBL), polyglycolide, polypropiolactone (PPL), and polytrimethylene carbonate.

Exemplary hydrophilic blocks can be selected from polymer segments formed from monomers such as ethylene glycol, ethylene oxide, vinyl alcohol, propylene oxide, vinyl pyrrolidone, hydroxy ethyl methacrylate, and hydroxy ethyl acrylate.

Exemplary hydrophilic blocks include (PEO), polyvinyl alcohol (PVA), poly(vinyl pyrrolidone) (PVP), polyacrylamide, poly(hydroxy alkyl methacrylate), poly(hydroxy ethyl methacrylate), hydrophilic polyurethane, HYPAN, oriented HYPAN, poly(hydroxy ethyl acrylate), poly(ethyloxazoline), and polyamines (e.g., Jeffamine™).

In some aspects the second polymer comprises a polyalkoxyalkane block. Representative examples of polyalkoxyalkane blocks include poly(ethylene glycol), tetraethylene glycol, triethylene glycol, trimethylolpropane ethoxylate, and pentaeerythritol etholxylate blocks.

Exemplary hydrophilic blocks have a molecular weight of about 100 Da to about 5000 Da, or about 250 Da to about 3500.

In some aspects, the degradable polymers include at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (Tg) of at most 37° C. (Tg) at physiological (body) conditions. The pre-polymers A and B can be a hydrolysable polyester, polyetherester, polycarbonate, polyestercarbonate, polyanhydride or copolymers thereof, derived from cyclic monomers such as lactide (L,D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers may be chosen in such a way that the maximum glass transition temperature of the resulting copolymer is below 37° C. at body conditions. To fulfill the requirement of a Tg below 37° C., some of the above-mentioned monomers or combinations of monomers may be more preferred than others. This may by itself lower the Tg, or the pre-polymer is modified with a polyethylene glycol with sufficient molecular weight to lower the glass transition temperature of the copolymer. The degradable multi-block copolymers can include hydrolysable sequences being amorphous and the segments may be linked by a multifunctional chain-extender, the segments having different physical and degradation characteristics. For example, a multi-block co-polyester consisting of a glycolide-ε-caprolactone segment and a lactide-glycolide segment can be composed of two different polyester pre-polymers. By controlling the segment monomer composition, segment ratio and length, a variety of polymers with properties that can easily be tuned can be obtained. Such degradable multi-block copolymers can specifically include those described in U.S. Publ. App. No. 2007/0155906, the content of which is herein incorporated by reference in its entirety.

Specific examples of these types of degradable copolymers include poly(ether ester) multiblock copolymers based on poly(ethylene glycol) (PEG) and poly(butylene terephthalate) (PBT) that can be described by the following general structure:

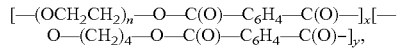

where —C$_6$H$_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. In embodiments, n can be selected such that the molecular weight of the PEG block is between about 300 and about 4000. X and y can be selected so that the multiblock copolymer contains from about 55% up to about 80% PEG by weight. The properties of copolymer can be changed by varying the values of n, x and y in the copolymer structure. An exemplary copolymer of this class is PEG$_{1000}$-45PBT-55 which is a copolymer of a poly(butyleneterephthalate-co-ethylene glycol) copolymer with 45 wt. % polyethylene glycol having an average molecular weight of 1000 kD and 55 wt. % butyleneterephthalate. PEG$_{1000}$-45PBT-55 is commercially available from OctoPlus (Leiden, Netherlands) under the product name PolyActive™.

Another example of these types of degradable copolymers include poly(ether ester) multiblock copolymers based on poly(ethylene glycol) (PEG) and one or more of glycolide, lactide, and/or caprolactone monomers or polymer segments. As specific example is 20GAPEGCL-80GALA, which is a block copolymer of 20 wt. % glycolide-polyethylene glycol-caprolactone "GAPEGCL" and 80 wt. % glycolide-lactide "GALA".

An initial step in the process of preparing the first particle aspect of the disclosure involves preparing a liquid composition including the bioactive agent and the first degradable biocompatible polymer. A solvent or solvent mixture can be chosen to dissolve both the bioactive agent and the first degradable biocompatible polymer.

Exemplary solvents or dispersant include, but are not limited to, aromatic hydrocarbons, such as benzene, xylene (e.g., ortho-xylene, para-xylene, or meta-xylene) and toluene; C1-C4 alcohols such as methanol, ethanol (EtOH), isopropanol (IPA), n-butanol, isobutyl alcohol and t-butyl alcohol; halogenated organic solvents such as dicholoroethane (DCE), dichloromethane (DCM), chloroform, and ethyl trifluroacetate (ETFA); ketones such as methyl isobutyl ketone (MIBK), 3-pentanone (diethyl ketone) acetone, 2-butanone (MEK); acetonitrile (ACN); ethers such as isopropyl ether (IPE) and tetrahydrofuran (THF); aliphatic hydrocarbons such as hexane, heptane, or the like; and esters such as ethyl acetate and butyl acetate.

An "acid group-containing polymer" refers to polymer that has acid groups presented on the polymer chain, and which can provide negatively charged groups to the particulate. Acidic groups include, for example, sulfonic acids, carboxylic acids, phosphonic acids, and the like. Exemplary salts of such groups include, for example, sulfonate, carboxylate, and phosphate salts. Exemplary counter ions include alkali, alkaline earths metals, ammonium, protonated amines, and the like. If one or more counter ions are used, the acid groups of the acid group-containing polymer can be partially neutralized.

Exemplary carboxylic acid-group containing monomers that can be used to prepare the acid group-containing polymer, include, but are not limited to, acrylic acid, methacrylic acid, itaconic acid, monomethyl itaconic acid, maleic anhydride, fumaric acid, and crotonic acid, and salts thereof. Exemplary sulfonic acid-group containing monomers that can be used to prepare the acid group-containing polymer, include, but are not limited to acrylamido-2-methylpropane-sulfonic acid (AMPS), 2-(meth)acrylamido-2-methylpropane sulfonic acid, vinyl sulfonic acid, 2-sulfoethyl methacrylate, and salts thereof. Other exemplary carboxylic acid-containing monomers that can be used to prepare the acid group-containing copolymers include styrene and maleic anhydride copolymerized to produce styrene-maleic anhydride copolymer (PSMA).

In various embodiments, the active agent composition includes a hydrophobic active agent and cationic delivery agent. While not wishing to be bound by theory, it is believed that the charge provided by the cationic delivery agents results in the composition being electrostatically attracted to negative charges and/or polar groups associated with the lipid bilayer present on or in a tissues or organs of a patient or charged/polar groups associated with the extracellular matrix (e.g., collagen, fibronectin, laminin, etc.). Consequently, combining an active agent, particularly a hydrophobic active agent with a cationic delivery agent in a composition for local administration can help retain the hydrophobic active agent near the site of administration. It is also thought that the cationic delivery agent may increase tissue permeability, thereby enhancing uptake of the active agent by the target tissue and/or organ.

In general, the upper limit for the amount of cationic delivery agent that is included in the active agent composition is guided by the toxicity limit for the given cationic delivery agent or the solubility of the cationic delivery agent in the aqueous carrier used in the composition. However, in one embodiment, the ratio of cationic delivery agent:hydrophobic active agent can be up to 1:1. The lower limit for the amount of cationic delivery agent that is included in the composition is guided by the efficacy of the composition. In general, the inventors have found that a ratio of cationic delivery agent:hydrophobic active agent of 1:50 and less has limited efficacy. Consequently, the composition generally has a ratio of cationic delivery agent: hydrophobic active agent of at least 1:25. In various embodiments, the ratio of cationic delivery agent:hydrophobic active agent is between about 1:1 and about 1:25. In another embodiment, the ratio of cationic delivery agent:hydrophobic active agent is at least about 1:2, 1:5 or 1:10 and up to about 1:10, 1:15, 1:20 or 1:25. In some embodiments, the composition herein includes at least about 0.1 mg/ml, 0.5 mg/ml, 1 mg/ml, 2 mg/ml, 3 mg/ml, 4 mg/ml, or 5 mg/ml and up to about 5 mg/ml, 10 mg/ml, 15 mg/ml, 20 mg/ml 25 mg/ml, 30 mg/ml, 35 mg/ml, 40 mg/ml or even about 45 mg/ml cationic delivery agent.

Cationic delivery agents used in embodiments herein include compounds containing a portion having a positive charge in aqueous solution at neutral pH along with a portion that can exhibit affinity for hydrophobic surfaces (such as hydrophobic or amphiphilic properties) and can therefore interface with hydrophobic active agents. In some embodiments, cationic delivery agents used in embodiments herein can include those having the general formula X-Y, wherein X is a positively charged group in aqueous solution at neutral pH and Y is a moiety exhibiting hydrophobic properties. In some embodiments, the cationic delivery agent can include a hydrophilic head and a hydrophobic tail, along with one or more positively charged groups, typically in the area of the hydrophilic head.

Cationic delivery agents can specifically include cationic lipids and net neutral lipids that have a cationic group. Exemplary lipids can include, but are not limited to, 313-[N—(N',N'-dimethylaminoethane)-carbamoyl] cholesterol hydrochloride (DC-cholesterol); 1,2-dioleoyl-3-trimethyl-ammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethyl-ammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE).

Cationic delivery agents can specifically include cationic polymers. Cationic delivery agents can also include polycation-containing cyclodextrin, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polypropylenimine, polyamidoamine dendrimers (PAMAM; available from Sigma Aldrich), cationic polyoxazoline, polyvinylamine (PVAm), and poly(beta-aminoesters). Cationic delivery agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers.

In various embodiments, the cationic delivery agent includes polyethylenimine (PEI). PEI is a basic cationic aliphatic polymer which can be linear or branched. PEI herein can specifically include water soluble PEI. Linear PEI is a solid at room temperature and includes predominantly secondary amines and is soluble in water at relatively low molecular weights. Branched PEIs are liquid at room temperature and include primary, secondary and tertiary amino groups and is typically soluble in water. The ratio of primary:secondary:tertiary amino groups reflects the amount of branching, wherein the relative amount of secondary amino groups decreases as the amount of branching increases. In various embodiments, PEI includes primary:secondary:tertiary amino groups at a ratio of between about 1:3:1 and 1:1:1, or between about 1:2:1 and 1:1:1. In another embodiment, PEI includes primary:secondary:tertiary amino groups at a ratio of between about 1:2:1 and 1:1:1, 1:1.1:1, 1:1.2:1, 1:1.3:1, 1:1.4:1, 1:1.5:1, 1:1.6:1, 1:1.7:1, 1:1.8:1, or 1:1.9:1. In another embodiment, PEI is linear and includes predominantly secondary amines. In various embodiments, branched PEI includes no more than about 30%, 35%, 40%, 45%, 50%, 55%, 60%, 65%, 70%, or 75% secondary amine groups. In other embodiments, PEI includes one or more quaternary amine groups.

In one method, PEI is synthesized from monomers that include a three-membered ring in which two corners of the molecule have (—$CH_2$—) linkages and the third corner includes a secondary amine group (=NH). In the presence of a catalyst the three-membered ring is converted into a highly branched polymer with about 25% primary amine groups, 50% secondary amine groups, and 25% tertiary amine groups. The branched polymers can be copolymerized to produce PEI having a variety of molecular weights, from 2 kD up to 5000 kD. In various embodiments, PEI has a molecular weight of at least about 25 kD, 50 kD, 70 kD, 75 kD, 100 kD, 150 kD, 200 kD, 250 kD, 300 kD, 350 kD, 400 kD, 450 kD, 500 kD, 550 kD, 600 kD, 650 kD, 700 kD, 750 kD, 800 kD, 850 kD, 900 kD, 950 kD or 1000 kD and up to about 1000 kD, 1500 kD, 2000 kD, 2500 kD, 3000 kD, 3500 kD, 4000 kD, 4500 kD or 5000 kD. Methods for synthesizing linear PEI are also known.

In other embodiments of the present disclosure, cationic delivery agents having a positive charge in aqueous solutions at neutral pH include the following Compounds (A-I):

Compound A
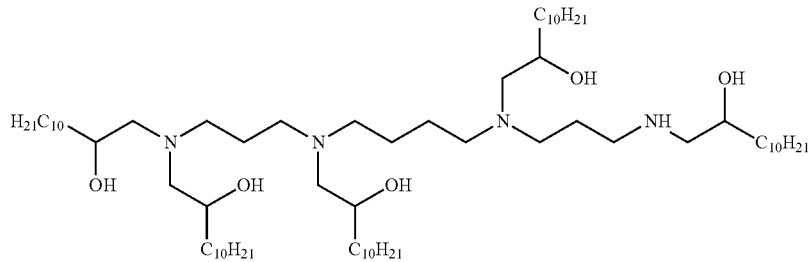
Compound B
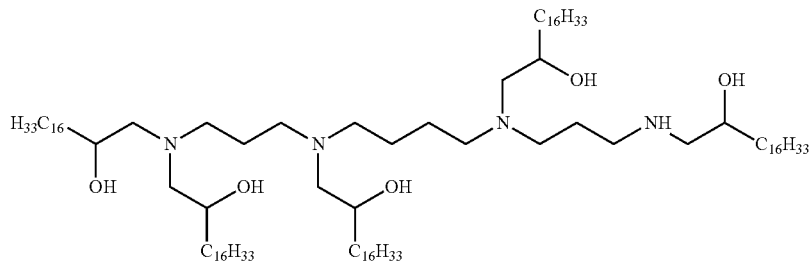
Compound C
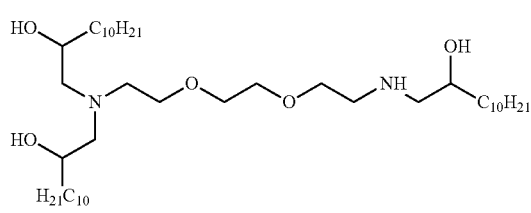
Compound D
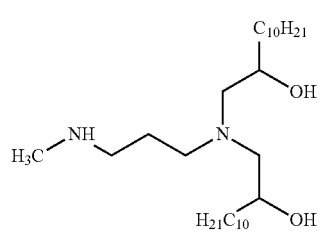
Compound E
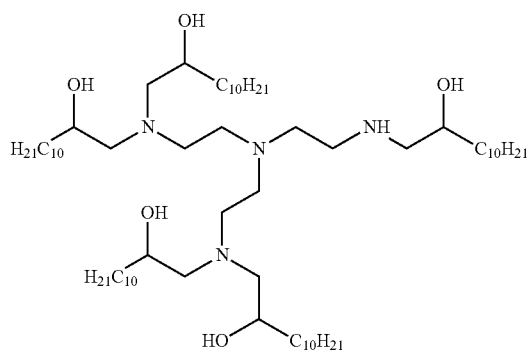
Compound F
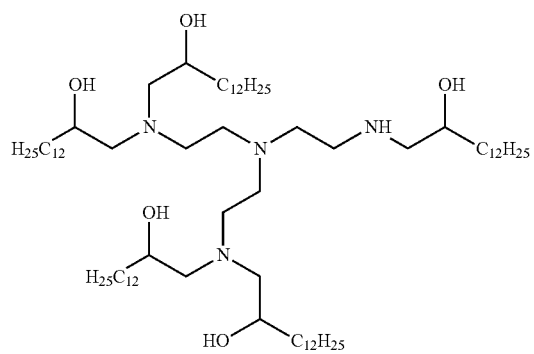
Compound G
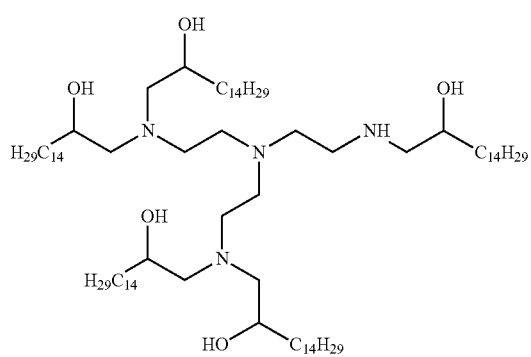
Compound H
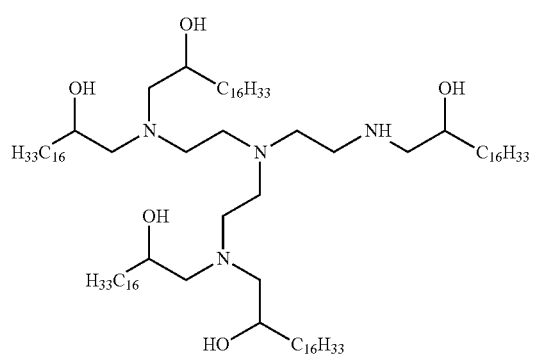

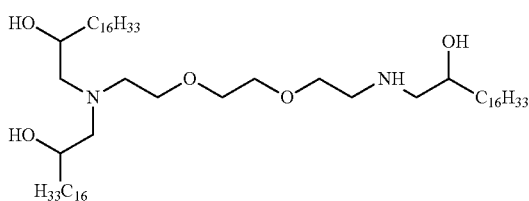

Compound I

Additionally, other cationic delivery agents include structures of the general Formula I:

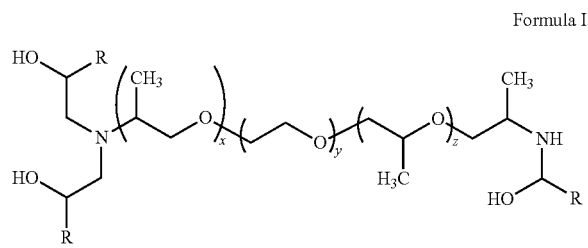

Formula I

TABLE 1

Values for Variables x + z,
y and R for Compounds J-R of Formula I.

| Compound | x + z | y | R |
|---|---|---|---|
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

Methods for making cationic delivery agents, such as those listed above, are described in more detail in U.S. patent application Ser. No. 13/469,844, entitled "DELIVERY OF COATED HYDROPHOBIC ACTIVE AGENT PARTICLES," the disclosure of which is hereby incorporated by reference herein in its entirety. In general, cationic delivery agents, such as those listed above, can generally be prepared by the reaction of an appropriate hydrophobic epoxide (e.g. oleyl epoxide) with a multi-functional amine (e.g. propylene diamine). Details of the synthesis of related cationic delivery agents are described by K. T. Love in the publication PNAS 107, 1864-1869 (2010) and Ghonaim et al., Pharma Res 27, 17-29 (2010).

It will be appreciated that polyamide derivatives of PEI (PEI-amides) can also be applied as cationic delivery agents. PEI-amides can generally be prepared by reacting PEI with an acid or acid derivative such as an acid chloride or an ester to form various PEI-amides. For example, PEI can be reacted with methyl oleate to form PEI-amides.

In yet other embodiments cationic delivery agents can include moieties used to condense nucleic acids (for example lipids, peptides and other cationic polymers). In some instances these cationic delivery agents can be used to form lipoplexes and polyplexes.

In other embodiments, the active agent compositions herein can include one or more additional components, such as a diluent, excipient, adjuvant, emulsifier, buffer, stabilizer, preservative, and the like. In various embodiments, the active agent composition includes one or more contrast agents, for example, an iodinated radiocontrast agent.

In another embodiment, the active agent compositions can include one or more agents that enhance tissue penetration, including, but not limited to zonulin, propylene glycol, mono-, di- or tri-glycerides etc.

Exemplary additive components can further include compounds that stabilize poorly water soluble pharmaceutical agents. Exemplary additive components providing such stabilization include biocompatible polymers, for example albumins. Additional additive components are described in U.S. Pat. No. 7,034,765 (De et al.), the disclosure of which is incorporated herein by reference. Stabilization of suspensions and emulsions can also be provided by compounds, for example, such as surfactants (e.g. F68).

Other additives include saccharides. Saccharides can include monosaccharides, disaccharides, trisaccharides, oligosaccharides, and polysaccharides. Polysaccharides can be linear or branched polysaccharides. Exemplary saccharides can include but are not limited to dextrose, sucrose, maltose, mannose, trehalose, and the like. Exemplary saccharides can further include, but are not limited to, polysaccharides including pentose, and/or hexose subunits, specifically including glucans such as glycogen and amylopectin, and dextrins including maltodextrins, fructose, mannose, galactose, and the like. Polysaccharides can also include gums such as pullulan, arabinose, galactan, etc.

Saccharides can also include derivatives of polysaccharides. It will be appreciated that polysaccharides include a variety of functional groups that can serve as attachment points or can otherwise be chemically modified in order to alter characteristics of the saccharide. As just one example, it will be appreciated that saccharide backbones generally include substantial numbers of hydroxyl groups that can be utilized to derivatize the saccharide. Saccharides can also include copolymers and/or terpolymers, and the like, that include saccharide and/or saccharide subunits and/or blocks.

Polysaccharides used with embodiments herein can have various molecular weights. By way of example, glycogen used with embodiments herein can have a molecular weight of greater than about 250,000. In some embodiments glycogen used with embodiments herein can have a molecular weight of between about 100,000 and 10,000,000 Daltons.

Refinement of the molecular weight of polysaccharides can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

It will be appreciated that polysaccharides such as maltodextrin and amylose of various molecular weights are commercially available from a number of different sources. For example, Glucidex™ 6 (avg. molecular weight ~95,000 Da) and Glucidex™ 2 (avg. molecular weight ~300,000 Da) are available from Roquette (France); and MALTRIN™ maltodextrins of various molecular weights, including molecular weights from about 12,000 Da to 15,000 Da are available from GPC (Muscatine, Iowa). Examples of other hydrophobic polysaccharide derivatives are disclosed in US Patent Publication 2007/0260054 (Chudzik), which is incorporated herein by reference.

In another embodiment, the composition includes one or more amphiphilic additive. Amphiphilic compounds include those having a relatively hydrophobic portion and a relatively hydrophilic portion. Exemplary amphiphilic compounds can include, but are not limited to, polymers including, at least blocks of, polyvinylpyrrolidone, polyvinyl alcohol, polyethylene glycol, polyoxazolines (such as poly (2-alkyloxazoline) and derivatives) and the like. Exemplary amphiphilic compounds can specifically include poloxamers. Poloxamers are nonionic triblock copolymers composed of a central hydrophobic chain of polyoxypropylene flanked by two hydrophilic chains of polyoxyethylene. Poloxamers are frequently referred to by the trade name PLURONIC®. It will be appreciated that many aspects of the copolymer can be varied such the characteristics can be customized. One exemplary poloxamer is PLURONIC® F68 (non-ionic, co-polymer of ethylene and propylene oxide commercially available from BASF Corporation; also designated as F68 and poloxamer F68), which refers to a poloxamer having a solid form at room temperature, a polyoxypropylene molecular mass of approximately 1,800 g/mol and roughly 80% polyoxyethylene content, with a total molecular weight of approximately 8,400 g/mol, the copolymer terminating in primary hydroxyl groups.

In yet other embodiments, additive components can further include additives that effectively reverse the effect of drug uptake in tissue. Exemplary components that induce this reversal effect include heparin and heparin derivatives. Other negatively charged additive components that can complex with the cationic delivery agent of the present disclosure can also provide this reversal effect.

In various embodiments, the active agent composition includes a hydrophobic active agent and a cationic delivery agent in a pharmaceutically acceptable carrier. In some embodiments, this can be an aqueous carrier. As used herein, a "pharmaceutically acceptable carrier" refers to a carrier or diluent that does not cause significant irritation to an organism and does not abrogate the biological activity and properties of the administered composition. In various embodiments, the aqueous carrier includes water or buffered saline. In a more particular embodiment, the aqueous carrier includes distilled water, double distilled water or distilled deionized water. In various embodiments, the hydrophobic active agent and/or the cationic delivery agent are suspended in water. In various embodiments, the carrier includes a minor amount (e.g., less than about 20%, 15%, 10%, 9%, 8%, 7%, 6%, 5%, 4%, 3%, 2% or 1%) of a biocompatible solvent. As used herein, the term "biocompatible solvent" refers to a solvent that is considered non-toxic and does not elicit an immunological response at the amounts included in the carrier. Examples of biocompatible solvents include, but are not limited to, ethanol, ethyl lactate, acetone, dimethyl-sulfoxide (DMSO), and combinations thereof. In various embodiments, the hydrophobic active agent is suspended in water as a coated therapeutic agent. In various embodiments, a mixing or agitation step can be performed in order to allow the hydrophobic active agent to interface with the cationic delivery agent. In some embodiments, the cationic delivery agent surrounds and/or encapsulates the particulate hydrophobic active agent to form a coated active agent particle.

In various embodiments, the pH of the composition is adjusted to at least about 5, 6 or 7 and up to about 7, 8 or 9.

Methods

Many different methods are contemplated herein, including, but not limited to, methods of making devices, methods of coating devices, and the like. Aspects of system/device operation described elsewhere herein can be performed as operations of one or more methods in accordance with various embodiments herein.

In an embodiment, a method of operating a coating system for coating a medical device is included, the method can include actuating a valve to assume a first fluid transport state wherein the valve provides fluid communication between a fluid supply reservoir and a reciprocating positive displacement pump, conveying a coating suspension from the fluid supply reservoir to the reciprocating positive displacement pump through a first fluid flow path (a "filling" or "refilling" operation), actuating the valve to assume a second fluid transport state wherein the valve provides fluid communication between the reciprocating positive displacement pump and a fluid applicator, and conveying the coating suspension from the reciprocating positive displacement pump to the fluid applicator through a second fluid flow path to allow the suspension to be coated onto a surface of a medical device (a "coating application" operation). The filling operation can be conducted for as long as it takes to fill a desirable amount of the coating suspension into the pump and is not particularly limited. However, in some cases, inconsistency in the coating process may occur if the coating application operation lasts too long depending on the nature of the suspension. In some embodiments, the coating application operation last less than about 60, 45, 40, 35, 30, 25, 20, 15, 10, or 5 minutes, or an amount of time falling within a range between any of the foregoing.

In an embodiment of the method, conveying the coating suspension from the reciprocating positive displacement pump to the fluid applicator through a second fluid flow path can include conveying a first volume of the coating suspension from the reciprocating positive displacement pump to the fluid applicator through the second fluid flow path, positioning the fluid applicator to be in contact with the medical device, and conveying a second volume of the coating suspension from the reciprocating positive displacement pump to the fluid applicator through the second fluid flow path.

In an embodiment of the method, the first volume is about 50 μl to about 100 μl. In an embodiment of the method, conveying a second volume of the coating suspension from the reciprocating positive displacement pump to the fluid applicator through the second fluid flow path is performed discontinuously for 15 to 30 minutes.

In an embodiment, the method can further include actuating the valve to assume the first fluid transport state wherein the valve provides fluid communication between the fluid supply reservoir and the reciprocating positive displacement pump, and returning the coating suspension (such as any remaining coating suspension) from the reciprocating positive displacement pump to the fluid supply reservoir through the first fluid flow path.

In an embodiment, the method can further include: mounting the medical device on a rotation mechanism, positioning the fluid applicator to be in contact with the medical device, and rotating the medical device with the rotation mechanism. conveying a coating composition from a fluid supply reservoir, through a fluid supply conduit, and through the two-part fluid applicator and onto a surface of the rotatable medical device.

In an embodiment, the method can further include agitating the coating suspension within the fluid supply reservoir.

In an embodiment of the method, the coating suspension can include an active agent, a cationic agent, and a liquid. In an embodiment of the method, the coating suspension can include sirolimus, polyethyleneimine (PEI), and water.

In an embodiment of the method, the weight ratio of sirolimus to PEI is from 90:10 to 99:1.

In an embodiment of the method, the concentration of sirolimus is about 150 mg/ml to 300 mg/ml.

In an embodiment of the method, the coating suspension can have a viscosity of about 5 to 30 centipoise at a shear rate of 300 [1/s].

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A coating system comprising:
   a valve;
   a fluid supply reservoir in fluid communication with the valve;
   a reciprocating positive displacement pump in fluid communication with the valve; and
   a fluid applicator in fluid communication with the valve;
   wherein the valve is configured to assume a first fluid transport state and a second fluid transport state;
   wherein the valve provides fluid communication between the fluid supply reservoir and the reciprocating positive displacement pump when in the first fluid transport state for filling of the reciprocating positive displacement pump;
   wherein the valve provides fluid communication between the reciprocating positive displacement pump and the fluid applicator when in the second fluid transport state for applying a coating suspension to a medical device surface;
   wherein the fluid supply reservoir, the valve, and the reciprocating positive displacement pump define a first fluid flow path, the first fluid flow path comprising an inner diameter of about 100 microns to about 500 microns;
   wherein the first fluid flow path substantially lacks expansional changes in cross-sectional area exceeding 10% and
   wherein a second fluid flow path substantially lacks expansional changes in cross-sectional area exceeding 10%.

2. The coating system of claim 1, wherein the first fluid flow path is at least about 2 centimeters in length.

3. The coating system of claim 1, wherein the first fluid flow path lacks cavities, wherein a cavity is a substantial increase of an effective cross-section of the first fluid flow path.

4. The coating system of claim 1, wherein the reciprocating positive displacement pump, the valve, and the fluid applicator define the second fluid flow path, the second fluid flow path comprising an inner diameter of about 100 microns to about 500 microns.

5. The coating system of claim 3, wherein the second fluid flow path is at least about 2 centimeters in length.

6. The coating system of claim 3, wherein the second fluid flow path lacks cavities, wherein a cavity is a substantial increase of an effective cross-section of the second fluid flow path.

7. The coating system of claim 1, wherein the second fluid flow path is substantially straight when the valve is in the second fluid transport state.

8. The coating system of claim 1, wherein the first fluid flow path and the second fluid flow path partially overlap.

9. The coating system of claim 1, wherein the reciprocating positive displacement pump is selected from the group consisting of a plunger pump, a piston pump, a diaphragm pump, and a syringe pump.

10. The coating system of claim 1, wherein the reciprocating positive displacement pump is at least one of a single-acting reciprocating pump and a syringe pump.

11. The coating system of claim 1, wherein the valve comprises a three-way valve.

12. The coating system of claim 11, wherein the three-way valve comprises at least one of a three-way stopcock, a ball valve, a T-port valve, and a L-port valve.

13. The coating system of claim 11, wherein the three-way valve comprises a pneumatic diaphragm actuator, a pneumatic piston actuator, or an electric actuator.

14. The coating system of claim 1, further comprising a rotation mechanism configured to mount and rotate a rotatable device to be coated.

15. The coating system of claim 14, further comprising a fluid applicator actuator to move the fluid applicator with respect to a rotation axis defined by the rotation mechanism.

16. The coating system of claim 14, further comprising a fluid applicator actuator configured to move the fluid applicator toward a rotation axis defined by the rotation mechanism and into contact with a rotatable medical device supported by the rotation mechanism.

17. The coating system of claim 1, further comprising a coating suspension disposed within the fluid supply reservoir.

* * * * *

UNITED STATES PATENT AND TRADEMARK OFFICE
CERTIFICATE OF CORRECTION

PATENT NO. : 11,478,815 B2
APPLICATION NO. : 17/149390
DATED : October 25, 2022
INVENTOR(S) : Chappa et al.

Page 1 of 1

It is certified that error appears in the above-identified patent and that said Letters Patent is hereby corrected as shown below:

On the Title Page

Please add the following Inventor in (72):
Alvin A. Kucera, Maple Grove, MN (US)

Signed and Sealed this
Twenty-seventh Day of June, 2023

Katherine Kelly Vidal
*Director of the United States Patent and Trademark Office*